United States Patent
Wang et al.

(10) Patent No.: US 11,490,830 B2
(45) Date of Patent: Nov. 8, 2022

(54) APPARATUS AND METHOD FOR QUANTIFICATION OF THE MAPPING OF THE SENSORY AREAS OF THE BRAIN

(71) Applicants: ARIZONA BOARD OF REGENTS ON BEHALF OF ARIZONA STATE UNIVERSITY, Scottsdale, AZ (US); OHIO STATE INNOVATION FOUNDATION, Columbus, OH (US)

(72) Inventors: Yalin Wang, Tempe, AZ (US); Duyan Ta, Gilbert, AZ (US); Zhong-Lin Lu, Dublin, OH (US)

(73) Assignees: ARIZONA BOARD OF REGENTS ON BEHALF OF ARIZONA STATE UNIVERSITY, Scottsdale, AZ (US); OHIO STATE INNOVATION FOUNDATION, Columbus, OH (US)

( * ) Notice: Subject to any disclaimer, the term of this patent is extended or adjusted under 35 U.S.C. 154(b) by 573 days.

(21) Appl. No.: 16/230,284

(22) Filed: Dec. 21, 2018

(65) Prior Publication Data
US 2019/0192039 A1 Jun. 27, 2019

Related U.S. Application Data

(60) Provisional application No. 62/609,704, filed on Dec. 22, 2017.

(51) Int. Cl.
*A61B 5/055* (2006.01)
*A61B 5/00* (2006.01)
(Continued)

(52) U.S. Cl.
CPC ............ *A61B 5/055* (2013.01); *A61B 5/0042* (2013.01); *A61B 5/4064* (2013.01);
(Continued)

(58) Field of Classification Search
CPC ..... A61B 5/055; A61B 5/0042; A61B 5/4064; G06T 7/0012; G06T 2207/10088;
(Continued)

(56) References Cited

U.S. PATENT DOCUMENTS

2016/0350979 A1* 12/2016 Zeng ...................... G06T 15/04

OTHER PUBLICATIONS

Weber, Ofir, Ashish Myles, and Denis Zorin. "Computing extremal quasiconformal maps." Computer Graphics Forum. vol. 31. No. 5. Oxford, UK: Blackwell Publishing Ltd, 2012. (Year: 2012).*
(Continued)

*Primary Examiner* — Christopher Koharski
*Assistant Examiner* — Remy C Cooper
(74) *Attorney, Agent, or Firm* — Michael Best & Friedrich LLP

(57) ABSTRACT

Method and systems provide a tool to quantify sensory maps of the brain. Cortical surfaces are conformally mapped to a topological disk where local geometry structures are well preserved. Retinotopy data are smoothed on the disk domain to generate a curve that best fits the retinotopy data and eliminates noisy outliers. A Beltrami coefficient map is obtained, which provides an intrinsic conformality measure that is sensitive to local changes on the surface of interest. The Beltrami coefficient map represents a function where the input domain is locations in the visual field and the output is a complex distortion measure at these locations. This function is also invertible. Given the boundaries and the Beltrami map of a flattened cortical region, a corresponding visual field can be reconstructed. The Beltrami coefficient map allows visualization and comparison of retinotopic map properties across subjects in the common visual field space.

8 Claims, 18 Drawing Sheets
(11 of 18 Drawing Sheet(s) Filed in Color)

(51) Int. Cl.
  *G06T 7/00* (2017.01)
  *G16H 30/40* (2018.01)
  *G01R 33/48* (2006.01)
  *G01R 33/56* (2006.01)
(52) U.S. Cl.
  CPC ........ *G06T 7/0012* (2013.01); *G01R 33/4806* (2013.01); *G01R 33/5608* (2013.01); *G16H 30/40* (2018.01)
(58) Field of Classification Search
  CPC ...... G06T 2207/30016; G01R 33/5608; G01R 33/4806; G16H 30/40
  See application file for complete search history.

(56) References Cited

OTHER PUBLICATIONS

Functional magnetic resonance imaging, Wikipedia, Wikimedia Foundation, modified Dec. 10, 2016, https://web.archive.org/web/20161214012539/https://en.wikipedia.org/wiki/Functional_magnetic_resonance_imaging. (Year: 2016).*
Galway, Lionel. "Spline models for observational data." (1992): 113-114. (Year: 1992).*
Zeng, Wei, et al. "Surface quasi-conformal mapping by solving Beltrami equations." IMA International Conference on Mathematics of Surfaces. Springer, Berlin, Heidelberg, 2009. (Year: 2009).*
Ta, Duyan. Characterizing Retinotopic Mapping Using Conformal Geometry and Beltrami Coefficient: a Preliminary Study. 2013. Arizona State University, M.S. thesis. https://repository.asu.edu/attachments/125985/content/Ta_asu_0010N_13294.pdf (Year: 2013).*
DeYoe et al., "Mapping striate and extrastriate visual areas in human cerebral cortex", Proceedings of the National Academy of Sciences, vol. 93, Mar. 1996, pp. 2382-2386.
Engel et al., "fMRI of human visual cortext", Nature, vol. 369, Jun. 1994, p. 525.
Engel et al., "Retinotopic organization in human visual cortex and the spatial precision of functional MRI", Cerebral Cortex, 7(2), Mar. 1997, pp. 181-192.
Hansen et al., "Parametric reverse correlation reveals spatial linearity of retinotopic human V1 BOLD response", Neuroimage, 23(1), 2004, pp. 233-241.
Sereno et al., "Borders of multiple visual areas in humans revealed by functional magnetic resonance imaging" Science, vol. 268, May 1995, pp. 889-893.
Vanni et al., "Multifocal fMRI mapping of visual cortical areas", Neuroimage, vol. 27, No. 1, 2005, pp. 95-105.
Schneider et al., "Functional topographic mapping of the cortical ribbon in human vision with conventional MRI scanners", Nature, vol. 365, Sep. 1993, pp. 150-153.
Tootell et al., "Functional analysis of human MT and related visual cortical areas using magnetic resonance imaging", The Journal of Neuroscience, vol. 15, No. 4, Apr. 1995, pp. 3215-3230.
Michel et al., "An illusion predicted by V1 population activity implicates cortical topography in shape perception", Nature Neuroscience, vol. 16, No. 10, Oct. 2013, pp. 1477-1483.
Schwarzkopf et al., "The surface area of human V1 predicts the subjective experience of object size", Nature neuroscience vol. 14, No. 1, Jan. 2011, pp. 28-30.
Brewer et al., "Visual cortex in aging and alzheimer's disease: changes in visual field maps and population receptive fields" Frontiers in Psychology, vol. 5, Article 74, Feb. 2014, pp. 1-16.
Wandell et al., "Imaging retinotopic maps in the human brain", Vision Research 51(7), 2011, pp. 718-737.
Dumoulin et al., "Population receptive field estimates in human visual cortex", Neuroimage 39(2), 2008, pp. 647-660.
Wandell et al., "Visual field map clusters in human cortex", Philosophical Transactions of the Royal Society of London B: Biological Sciences, 360(1456), Apr. 2005, pp. 693-707.
Qiu et al., "Estimating linear cortical magnification in human primary visual cortex via dynamic programming", Neuroimage vol. 31, No. 1, 2006, pp. 125-138.
Schwartz, "The development of specific visual connections in the monkey and the goldfish: Outline of a geometric theory of receptotopic structure", Journal of Theoretical Biology, vol. 69, No. 4, 1977, pp. 655-683.
Balasubramanian et al., "The V1-V2-V3 complex: quasiconformal dipole maps in primate striate and extra-striate cortex", Neural Networks 15(10), 2002, pp. 1157-1163.
Polimeni et al., "Multi-area visuotopic map complexes in macaque striate and extra-striate cortex", Vision research vol. 46, No. 20, 2006, pp. 3336-3359.
Torgerson, "Multidimensional scaling: I. Theory and Method", Psychometrika vol. 17, No. 4, Dec. 1952, pp. 401-419.
Shepard, "The analysis of proximities: Multidimensional scaling with an unknown distance function II", Psychometrika vol. 27, No. 3, 1962, pp. 219-246.
Kruskal, "Nonmetric multidimensional scaling: a numerical method", Psychometrika vol. 29, No. 2, Jun. 1964, pp. 115-129.
Kruskal, "Multidimensional scaling by optimizing goodness of fit to a nonmetric hypothesis", Psychometrika Vo. 29, No. 1, pp. 1-27.
Schwartz et al., "A numerical solution to the generalized mapmaker's problem: flattening nonconvex polyhedral surfaces", IEEE Transactions on Pattern Analysis and Machine Intelligence vol. 11, No. 9, Sep. 1989, pp. 1005-1008.
Balasubramanian et al., "Exact geodesics and shortest paths on polyhedral surfaces", IEEE transactions on Pattern Analysis and Machine Intelligence, vol. 31, No. 6, Jun. 2009, pp. 1006-1016.
Balasubramanian et al., "Near-isometric flattening of brain surfaces", NeuroImage vol. 51, No. 2, 2010, pp. 694-703.
Schira et al., "Two-dimensional mapping of the central and parafoveal visual field to human visual cortex", Journal of neurophysiology, vol. 97, No. 6, Mar. 2007, pp. 4284-4295.
Hurdal et al., "Cortical cartography using the discrete conformal approach of circle packings", NeuroImage 23, 2004, pp. S119-S128.
Hurdal et al., "Discrete conformal methods for cortical brain flattening", Neuroimage vol. 45, No. 1, 2009, pp. S86-S98.
Schira et al., "The foveal confluence in human visual cortex", Journal of Neuroscience, vol. 29, No. 28, Jul. 2009, pp. 9050-9058.
Lui et al., "Detection of shape deformities using yamabe flow and beltrami coefficients", Inverse Problems and Imaging, vol. 4, No. 2, 2010, pp. 311-333.
Brewer et al., "Visual field maps and stimulus selectivity in human ventral occipital cortex", Nature neuroscience, vol. 8, No. 8, Aug. 2005, pp. 1102-1109.
Wang et al., "Intrinsic brain surface conformal mapping using a variational method", Proceedings of SPIE, 2004, vol. 5370, pp. 241-252.
Ta et al., "Characterizing human retinotopic mapping with conformal geometry: a preliminary study" Medical Imaging: Image Processing, 2014, p. 90342A.
Su et al., "Area Preserving Brain Mapping", CVPR, Jun. 2013, pp. 2235-2242.

* cited by examiner

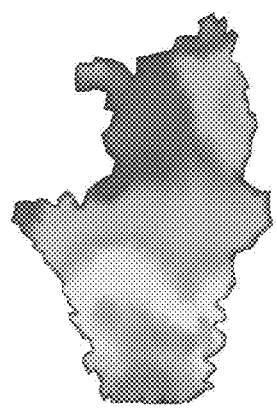
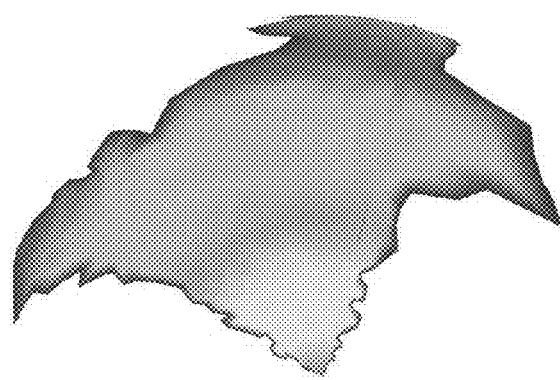
FIG. 5A            FIG. 5B            FIG. 5C
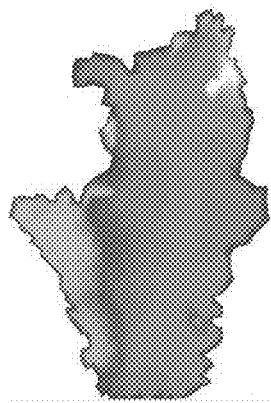
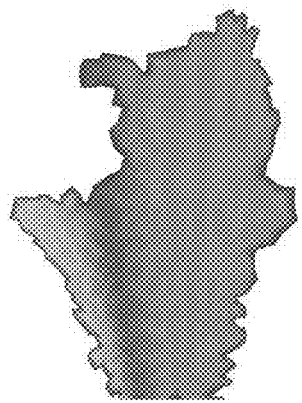
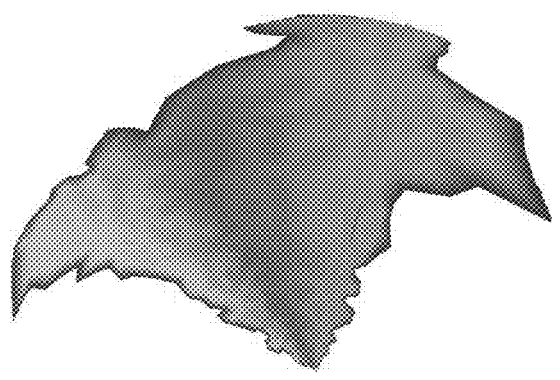
FIG. 5D            FIG. 5E            FIG. 5F Beltrami Coefficient Map

APPARATUS AND METHOD FOR QUANTIFICATION OF THE MAPPING OF THE SENSORY AREAS OF THE BRAIN

CROSS REFERENCE TO RELATED APPLICATIONS

This application is a non-provisional of and claims the benefit of U.S. Provisional Patent Application No. 62/609,704, filed on Dec. 22, 2017, which is hereby incorporated by reference in its entirety.

STATEMENT REGARDING FEDERALLY SPONSORED RESEARCH OR DEVELOPMENT

This invention was made with government support under 1413417 and 1412722 awarded by the National Science Foundation. The government has certain rights to the invention.

BACKGROUND

The sensory areas of the brain, including the auditory cortex, visual cortex, somatosensory cortex, and olfactory cortex, contain topographical representations of the sensory space. The increase in the quantity and quality of functional magnetic resonance imaging (fMRI) signals in the sensory cortices due to improved MRI resolution and experimental procedures have produced very detailed subject-specific cortical field maps. For example, retinotopic mapping of human visual cortex can generate cortical maps of the visual space by analyzing the stimulus-referred fMRI responses in each voxel of the MR image. The maps elucidate the spatial organization of the neuronal responses to visual images on the retina.

In clinical settings, doctors require quantitative scores. The current mapping methods of the sensory areas of the human brain can only generate qualitative maps, not quantitative scores. A medical imaging tool has yet to be developed to completely quantify the maps and compare the maps across time and/or individuals.

A growing number of neuroscientific studies have adopted their usage. They have transformed our understanding of the human visual system and the development of human cerebral cortex. They also hold great promises to further the understanding of plasticity in the human visual cortex and thus improve the rehabilitation efficacy on various visual function loss patients. Prior retinotopic mapping studies have been mainly devoted to discovering various visual areas and their roles in the visual processing pathway. The goal was mainly identification of visual areas based on experimental evidence of activated cortical areas. Further research is needed, that builds mathematically rigorous computation models that fully consider the intrinsic geometrical features of the underlying cortical structures to quantify retinotopic maps. Constructing a model that considers the underlying surface geometry would be more powerful because reconstructing missing or corrupted data is possible even when a large portion of data is missing or inconsistent causing statistical-based methods for reconstruction to fail. This is possibly true when areas of the visual cortex are damaged by disease or physical trauma. It can also be used to better handle typical functional data from retinotopic studies that suffers from many data artifacts. They break the generally consistent patterns expected of the mappings.

A complex logarithmic mapping, which is an angle preserving (conformal) mapping, was proposed to describe the primary visual cortex (V1) in macaque. Later, the Wedge-Dipole model composed a mapping including a non-conformal wedge mapping followed by a conformal dipole mapping to form a bounded conformal mapping (quasiconformal). These models are conformal from construction and not on direct measurement of the data from retinotopic mappings. Adjusting the free parameters in the model will best fit it to the functional data on the flattened cortical surface and indirectly measure the degree of angle preserving of the map. An important feature of previous approaches was to apply multidimensional scaling method (MDS) to compute near-isometric mapping from the original brain surface to the Euclidian plane for fitting the model to the data. However, the drawback of MDS is that it does not consider any surface geometric features and the results are only an approximation of the isometric mapping. Inevitably, the flattening procedure introduces many distortions that make the subsequent analysis inaccurate.

Over the years, several new models have been proposed to solve some counterintuitive predictions in Schwartz's model. Later, a hyperbolic conformal map of V1 using the circle packing method was computed. However, the mapping was only used for visualization and no quantitative models were developed to describe and compare the retinotopic maps. There are a number of issues: (1) large distortions are usually introduced in the cortical flattening process; (2) although the current method generates maps, there is no concrete mathematical description of these maps of visual space, and no direct way to quantitatively compare them. These difficulties have made retinotopic mapping mainly an experimental study in which data obtained in small samples pose significant challenges for a population level integration and analysis. Because of the lack of theoretical model, research on retinotopic mapping is strongly limited by available experimental protocols. For example, some large veins close to the fovea in many subjects significantly diminish the fMRI response accuracy and distort the retinotopic map. This problem is alleviated only recently with high resolution fMRI and optimized methods.

SUMMARY

Retinotopic maps are foundational to visual neuroscience because they spatially link the visual input representations in the retina to the cortical representation. Our results show that a retinotopic map is not a perfectly angle preserving map but rather a bounded angle distortion map. Our results demonstrate that conformality differences exist between individuals and they can be measured to reflect small local changes of retinotopically organized regions. The computed computational framework is coherent and computationally efficient and may become a standard protocol to analyze human retinotopic maps.

The present disclosure relates to an imaging method and system that provides a tool for quantitative description of sensory maps and therefore imaging scores that are important for disease diagnosis and prognosis of the human brain. The tool can be used to quantify plasticity and pathology in the sensory areas of the human brain that are associated with normal and abnormal development, aging, and diseases in sensory systems. The first application of the tool on retinotopic maps of the visual cortex has generated some excellent results.

The invention is built on a solid geometry theoretical foundation, computational conformal geometry, and brain MRI image analysis. The invention considers the intrinsic surface structure of the brain based on strong theoretical developments in differential geometry. The invention develops both a number of deep geometry concepts and practical computational algorithms for implementation.

In addition to retinotopic maps in V1, the embodiments of the invention also can be applied to all the other sensory areas, including higher level visual areas (V2, V3d, V3v, V4, MT, LOC, IT, FEF, etc.), auditory cortex, somatosensory cortex, and olfactory cortex.

In some embodiments, a method of quantifying the mapping of sensory areas of the brain comprises acquiring functional magnetic resonance imaging data of a patient to generate sensory data and a cortical map. A spherical conformal mapping process is applied to flatten cortical surfaces in the cortical map to a unit disk. Noise is removed in the cortical map. An approximate model of the sensory data is generated. A Beltrami coefficient map is generated based on the model of sensory data. A quasiconformal map is reconstructed based on the Beltrami coefficient map. A numerical metric is generated based on the quasiconformal map. A sensory projection of the quasiconformal map is reconstructed. A treatment is delivered to the patient based on the sensory projection.

In some embodiments, a method for using an area preserving surface flattening method comprises removing noise in sensory data of a magnetic resonance imaging (MRI) captured cortical map. A Beltrami coefficient map is generated based on sensory data. A quasiconformal map is generated based on the Beltrami coefficient map. A numerical metric is generated based on the quasiconformal map. A sensory projection of the quasiconformal map is generated. Treatment is delivered to the patient based on the numerical metric.

In some embodiments, a system for quantifying the mapping of sensory areas of the brain comprises an electronic processor coupled to a memory. The memory stores instructions that when executed by the electronic processor, cause the electronic processor to retrieve sensory functional magnetic resonance imaging (fMRI) data from a subject. A sensory cortical map is generated based on the sensory fMRI data. Brain structure MRI scan data is retrieved for the subject. The sensory cortical map and the brain structural scan data are normalized to a visual field disk space by conformally mapping the brain structural MRI scan data to a topological disk. The sensory fMRI data is smoothed on the disk by generating a curve that fits the sensory fMRI data and eliminates noisy outliers. A Beltrami coefficient map is generated, that comprises a Beltrami coefficient for each of a plurality of locations in the visual field disk space. Each Beltrami coefficient is based on a location in the visual field disk space and provides a distortion measure for the location in the disk space.

In some embodiments, a method of decoding Beltrami map values of activated regions within sensory areas of the brain to reconstruct the visual field stimuli comprises acquiring functional magnetic resonance imaging data of a patient to generate sensory data. A Beltrami coefficient map of a patient is updated with regional activation sensory data of interest. A quasiconformal map is reconstructed based on the Beltrami coefficient map. A sensory projection of the quasiconformal map is reconstructed.

In some embodiments, the sensory projection of the quasiconformal map can be used to guide rehabilitation procedures for cortical deficits, including cortical blindness and other cortical deficits. The sensory projection of the quasiconformal map can be used to guide surgery procedures. The sensory projection of the quasiconformal map can be used to decode brain signals captured by fMRI. The sensory projection of the quasiconformal map can be used to decode maps between different cortical areas.

In some embodiments, a system for decoding Beltrami map values of activated regions within sensory areas of the brain to reconstruct the visual field stimuli comprises an electronic processor coupled to a memory. The memory stores instructions that when executed by the electronic processor cause the electronic processor to retrieve sensory functional magnetic resonance imaging (fMRI) data from a subject. A sensory cortical map based on the sensory fMRI data is generated by the electronic processor. The electronic processor further retrieves brain structure MRI scan data for the subject. The electronic processor normalizes the sensory cortical map and the brain structural scan to a visual field disk space by conformally mapping the brain structural MRI scan data to a topological disk, and smooths the sensory fMRI data on the disk by generating a curve that fits the sensory fMRI data and eliminates noisy outliers. The electronic processor retrieves the baseline Beltrami coefficient map stored in memory for the subject, and generates a new Beltrami coefficient map comprising a Beltrami coefficient for each of a plurality of locations in the visual field disk space. Each Beltrami coefficient is based on a location in the visual field disk space and provides a distortion measure for the location in the disk space. A difference map is generated between the new Beltrami coefficient map and the baseline Beltrami coefficient map stored in memory for the subject. A sensory projection image is generated using the new Beltrami coefficient map. In some embodiments, the sensory projection image of the subject can be compared to prior baselines of the same subject or other subjects in the normalized disk space.

Other aspects of the disclosure will become apparent by consideration of the detailed description and accompanying drawings.

BRIEF DESCRIPTION OF THE DRAWINGS

The patent or application file contains at least one drawing executed in color. Copies of this patent or patent application publication with color drawing(s) will be provided by the United States Patent Office upon request and payment of the necessary fee.

FIGS. 5A-5F illustrate measured retinotopic data for eccentricity and polar angles that are smoothed using B-spline curve fitting, in accordance with some embodiments.

DETAILED DESCRIPTION

Figure 1:
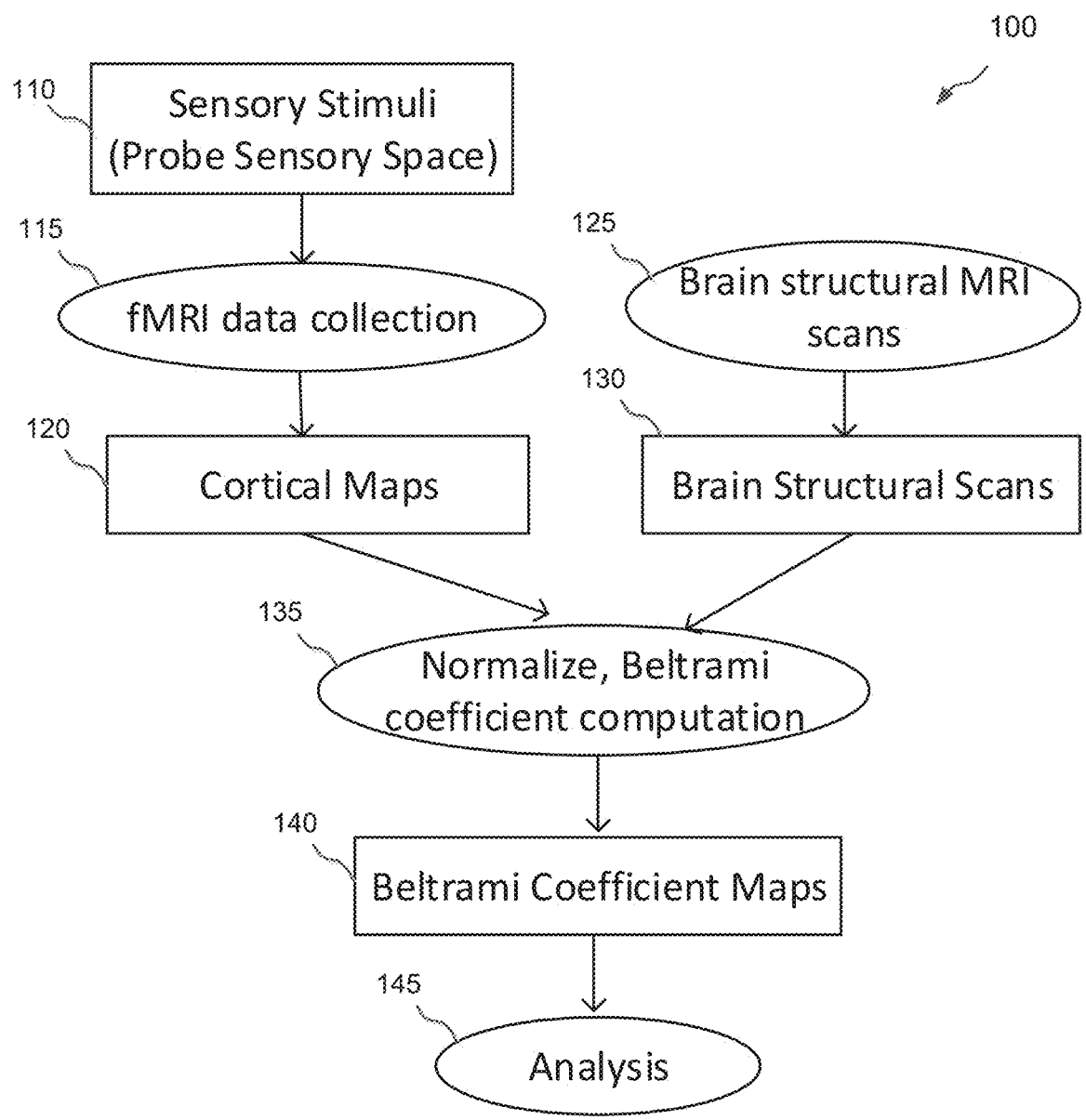
FIG. 1. Illustrates an overall pipeline for sensory mapping to cortical surface and Beltrami coefficient map visualization for visual cortical areas, in accordance with some embodiments.

Before any embodiments of the disclosure are explained in detail, it is to be understood that the disclosure is not limited in its application to the details of construction and the arrangement of components set forth in the following description or illustrated in the following drawings. The disclosure is capable of other embodiments and of being practiced or of being carried out in various ways.

It should be noted that a plurality of hardware and software based devices, as well as a plurality of different structural components may be utilized to implement embodiments described herein. In addition, it should be understood that embodiments described herein may include hardware, software, and electronic components or modules that, for purposes of discussion, may be illustrated and described as if the majority of the components were implemented solely in hardware. However, one of ordinary skill in the art, and based on a reading of this detailed description, would recognize that, in at least one embodiment, the electronic based aspects of embodiments described herein may be implemented in software (for example, stored on non-transitory computer-readable medium) executable by one or more processors. As such, it should be noted that a plurality of hardware and software based devices, as well as a plurality of different structural components may be utilized to implement the described embodiments. For example, "controllers," "logic," "generators," or "interfaces" described in the specification may include one or more electronic processors, one or more memory modules including non-transitory computer-readable medium, one or more input/output interfaces, and various connections (for example, a system bus) connecting the components. In some instances, the controllers described in the specification may be implemented in one of or a combination of a general processor, an application specific integrated circuit (ASIC), a digital signal processor (DSP), a field programmable gate array (FPGA), or the like.

A geometrically powerful way to describe 2 dimensional (2D) surface mappings is with quasi angle-preserving (quasiconformal) maps. Local angle-preserving maps preserve the shape geometry within each small domain and therefore exhibit less distortion overall than non-conformal maps. Angle-preserving (conformal) and quasiconformal maps for 2D surfaces is very well formulated and studied under Riemannian geometry. The angular distortions of these maps are described by the Beltrami coefficient (BC). In differential geometry, a conformal mapping is equivalent to solving the Beltrami equation where the solution is the BC is zero everywhere. It has been previously proposed for detecting irregular brain morphometry but has never been applied to retinotopic data. Quasiconformal (QC) maps provide a richer space of possible mappings than conformal maps because they relax the full angle-preserving requirement of conformal maps to allow for angle distortion up to a specified bound. These maps are appealing because they guarantee many properties of conformal maps but are more flexible due to the relaxed constraint. They are smooth, preserve angles, and are locally injective by construction.

The visual field can be geometrically regarded as a planar disk while the cortical surface a folded planar surface. Although the brain is a 3 dimensional (3D) object, the cortical surface can be represented as a closed 2D surface that is topologically equivalent to a spherical surface. Given two surfaces the BC between them can be measured and used to construct a QC mapping that describes the intrinsic shape of the data. In this sense, the BC and the QC map is a template for capturing and reconstructing retinotopic data. An issue with applying the BC to measure the mapping between the primary visual cortex and retinotopic data is functional data artifacts. Although functional magnetic resonance imaging (fMRI) has excellent spatial and temporal resolution, there are a significant number of artifacts that appear regularly with retinotopic data. Typical surface mappings require the topology to be preserved, that is adjacent points before the mapping must remain adjacent after the mapping and in the same ordering. In other words, the surface can be stretched like a rubber sheet but it cannot be torn. Artifacts make the travelling wave data inconsistent and therefore will alter the topology after the mapping.

The original Schwartz model is perfectly conformal for V1 while subsequent models introduce shear into the conformal model to better fit the fMRI data. These QC models are constructed using a composition of conformal and shear functions and have bounded conformality.

The activated neural patterns in the early cortical visual areas are angle-distorted maps of visual input patterns captured by the retinal surface. These maps are important because they characterize how the brain represents spatial information for processing and they are useful to improve the rehabilitation efficacy on various visual function loss patients.

Although numerous studies have been devoted to retinotopic mapping, most of them have taken an experimental approach to discover various visual areas and studied the relationship between them. Thus far, no concrete quantification models have been studied causing tremendous difficulties for making assertions about individual and group deviations from normal, if they exist. Missing at this time is a mathematical model that fully considers the intrinsic geometrical features of the underlying cortical structures. Instead, most studies have focused on 2D mappings but major distortions have been introduced when the 3D cortical surface is flattened to the 2D. A typical retinotopic map is usually generated in three steps: (1) flatten the cortical surfaces using structural scans; (2) project the functional data onto the flattened surfaces; (3) generate a phase map of the visual field on the flattened surface based on functional activations by visual stimuli on the retina. However, there are a number of issues, such as, for example: (1) large distortions are usually introduced in the cortical flattening process; (2) although the prior method generates maps, there is no concrete mathematical description of these maps and no direct way to quantitatively compare the maps across individuals or across time. These difficulties have made retinotopic mapping mainly an experimental study in which data obtained in small samples pose significant challenges for a population level integration and analysis. Because of the lack of a theoretical model, research on retinotopic mapping is strongly limited by available experimental protocols. For example, some large veins close to the fovea in many subjects significantly diminish the fMRI response accuracy and distort the retinotopic map. This problem is alleviated only recently with high resolution fMRI and optimized methods.

The present disclosure is built on a solid geometry theoretical foundation, computational conformal geometry, and brain MRI image analysis. This disclosure considers the intrinsic surface structure of the brain based on strong theoretical developments in differential geometry. This disclosure develops both a number of deep geometry concepts and practical computational algorithms for implementation.

Using computational conformal geometry, a method and system are disclosed for a tool to quantify sensory maps of the human brain. In its first implementation, embodiments of the disclosure conformally map visual cortical surfaces to a topological disk where local geometry structures are well preserved. Then, the retinotopy data are smoothed on the disk domain using a robust data smoothing method that generates a curve that best fits the retinotopy data and eliminates noisy outliers. Then, this curve is fitted with a piecewise polynomial B-spline function with an adjustable curve smoothness parameter to allow manual control in refining the curve to optimally fit the data while maintaining curve convexity. Finally, a Beltrami coefficient map is obtained, which is an intrinsic conformality measure that is sensitive to local changes on the surface of interest. The Beltrami coefficient map represents a function where the input domain is locations in the visual field and the output is a complex distortion measure at these locations. This function is also invertible in that given the boundaries and the Beltrami map of a flattened cortical region, the exact corresponding visual field can be reconstructed. In that sense, it is a complete description of the retinotopic data. More importantly, the Beltrami coefficient map allows visualization and comparison of the properties of the retinotopic maps across subjects in the common visual field space. Such comparison would enable comparison and quantification of the difference of retinotopic maps across subjects (people with and without a visual disease such as glaucoma), and across time (change of the map due to disease or treatment). Subjects, e.g., patients of glaucoma, are scanned with fMRI. Different from prior-art work, this disclosure makes use of intrinsic geometric features so the measures are more accurate. Furthermore, the Beltrami coefficient map can also be used to decode the activated brain signals as a result of retinal stimulation, i.e., one can recover the images being projected onto retinas by analyzing Beltrami coefficient maps. This is done by constructing a Beltrami coefficient map from the brain signals of the test subject which is a mosaic representation of the original sensory image in the sensory field and then inverting the map to recover the original sensory image. The inversion of the Beltrami map is done by constructing and solving a set of linear equations found in literature called the Linear Beltrami Solver (LBS). The Beltrami coefficient map and the boundary of the shape that is the visual area on the cortical surface are fixed parameters while the visual field locations of points on the shape are the unknown parameters. The LBS equations from literature are summarized below.

$$\sum_{T \in N_i} A_i^T [\alpha_1(T) a_T + \alpha_2(T) b_T] + B_i^T [\alpha_2(T) a_T + \alpha_3(T) b_T] = 0$$

$$\sum_{T \in N_i} A_i^T [\alpha_1(T) c_T + \alpha_2(T) d_T] + B_i^T [\alpha_2(T) c_T + \alpha_3(T) d_T] = 0$$

The Beltrami coefficients are computed per face of the discrete mesh representations of the cortical surface. Each face is represented as T in the equations below and $N_i$ is the set of faces incident to a vertex in the mesh. The quantities $A_i^T$ and $B_i^T$ are cotangent weights of each face with vertices $(v_i, v_j, v_k)$.

$A_i^T = (h_j - h_k)/2\text{Area}(T)$ $A_j^T = (h_k - h_i)/2\text{Area}(T)$ $A_k^T = (h_i - h_j)/2\text{Area}(T)$ $B_i^T = (g_j - g_k)/2\text{Area}(T)$ $B_j^T = (g_k - g_i)/2\text{Area}(T)$ $B_k^T = (g_i - g_j)/2\text{Area}(T)$ The quantities $a_T$, $b_T$, $c_T$, $d_T$ are derived by writing the Beltrami coefficient in terms of the approximate partial derivatives at each face as found in literature. They are defined for each face T with vertices $(v_i, v_j, v_k)$. Let $w_I = f(v_I)$ and I=i, j, or k and suppose $v_I = g_I + \sqrt{-1} h_I$ and $w_I = s_I + \sqrt{-1} t_I$ then.

$a_T = A_i^T s_i + A_j^T s_j + A_k^T s_k$ $b_T = B_i^T s_i + B_j^T s_j + B_k^T s_k$ $c_T = A_i^T t_i + A_j^T t_j + A_k^T t_k$ $d_T = B_i^T t_i + B_j^T t_j + B_k^T t_k$

In addition to retinotopic maps in V1, the embodiments of the disclosure also can be applied to all the other sensory areas, including higher level visual areas (V2, V3d, V3v, V4, MT, LOC, IT, FEF, etc.), auditory cortex, somatosensory cortex, and olfactory cortex.

Figure 2:
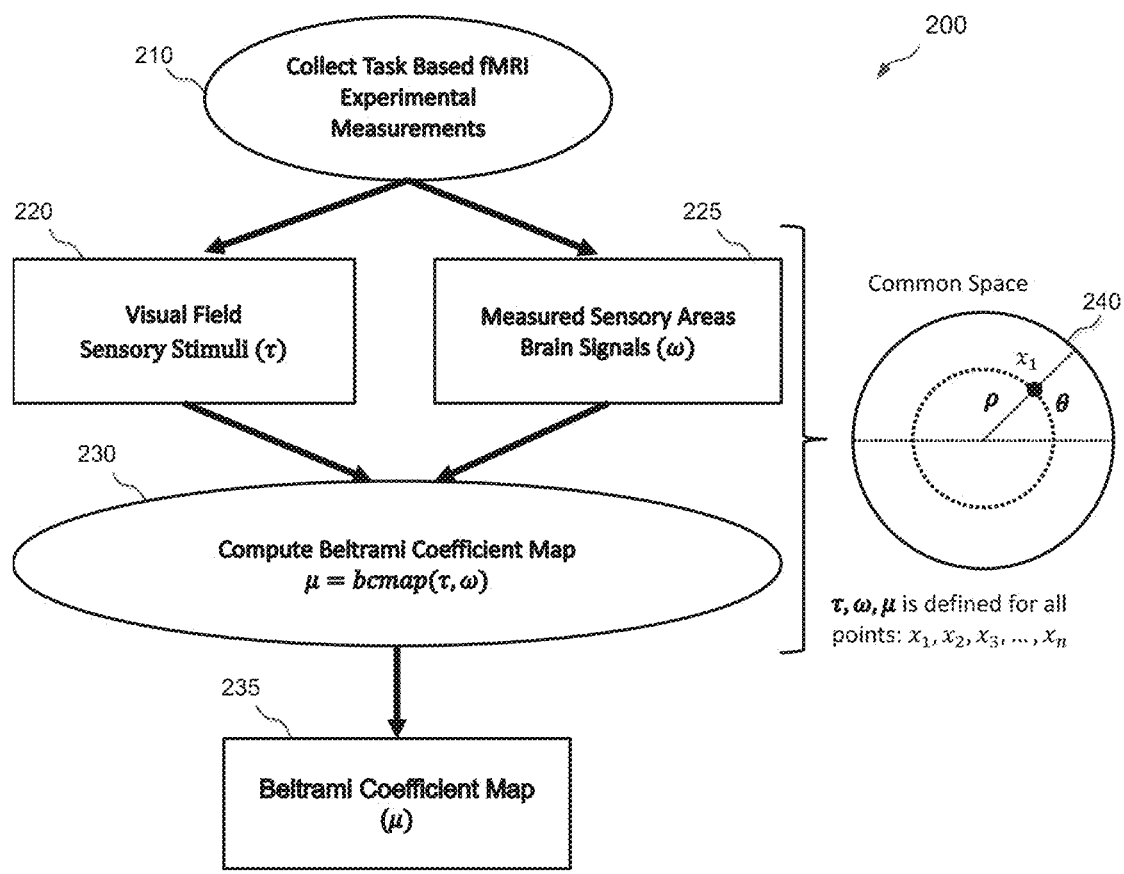
FIG. 2 illustrates an overall pipeline for sensory mapping decoding with Beltrami coefficient map visualization, in accordance with some embodiments.
Figure 3:
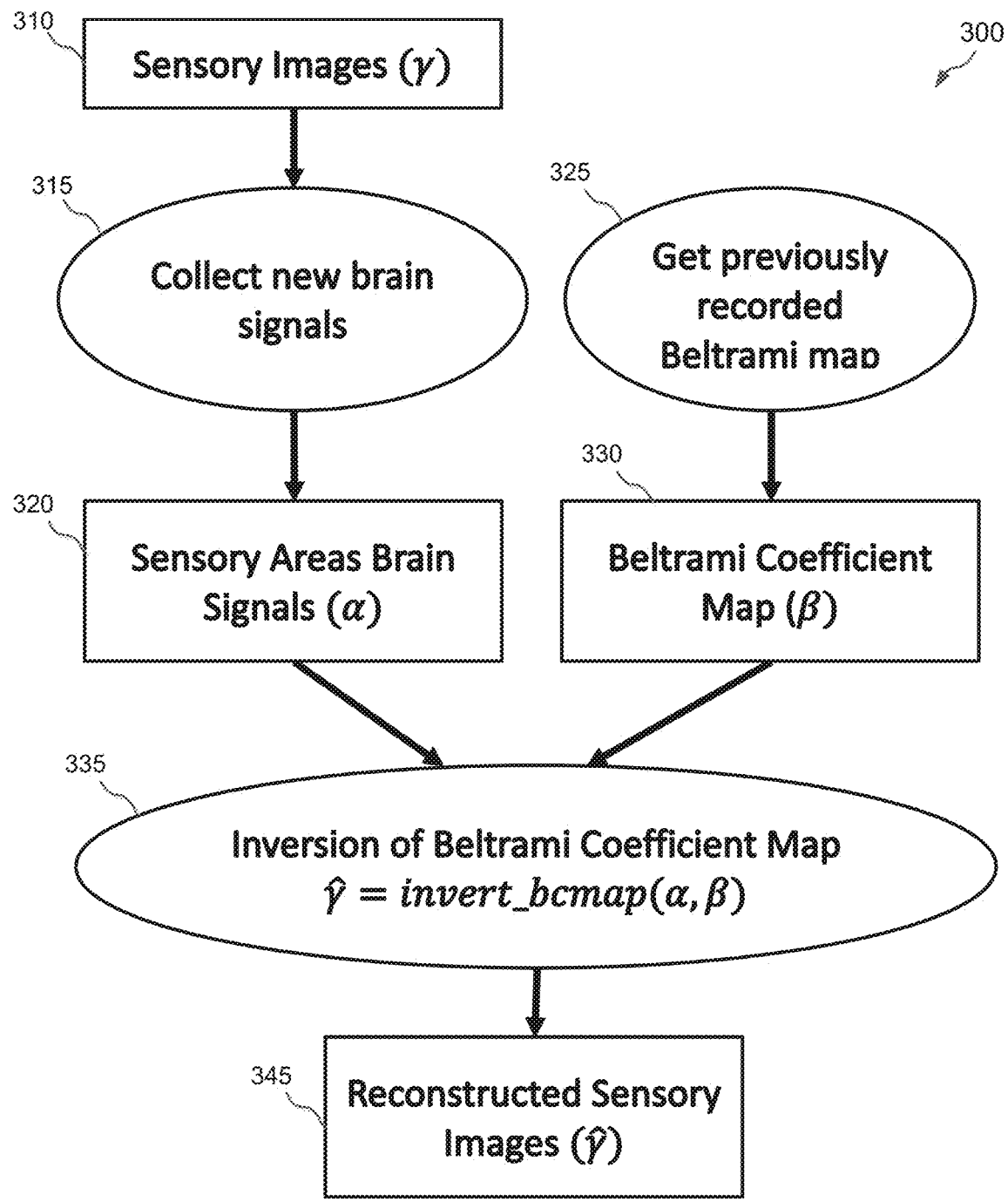
FIG. 3 illustrates an overall pipeline for brain sensory field decoding with Beltrami coefficient map visualization, in accordance with some embodiments.

With reference to FIGS. 1-3, embodiments of the present disclosure provide a framework for directly measuring the local surface geometry of individual retinotopic maps using the BC. A computationally efficient electronic processing methodology is provided that uses data clustering to discard artifacts and extract the most consistent traveling wave pattern. A B-spline is used to best fit the data. The measured BC and QC theory provides the necessary components for reconstructing consistent maps that fully describe retinotopy. The resulting individualized maps provide a reference baseline that can be further refined to fully characterize population retinotopy. Varying degrees of conformality have many useful properties regarding optimal mappings. It may provide key insights into biologically optimal organizational structures of visual cortex.

The functional data artifacts typical with retinotopic data were resolved using data clustering to extract the most consistent traveling wave pattern and best fit the data with a B-spline curve. This pre-processing step is critical for obtaining consistent traveling wave pattern to consistently map the vertices of the cortical surface mesh to the visual field space while preserving the topology. The conformality of retinotopic maps were measured using the BC, a measure that is sensitive to local changes between surfaces, to measure the angle preserving property of retinotopic maps. This method and system generates a map of BC for every vertex in the measured visual area. The BC map describes the angle preserving property and provides a reference template for modeling the expected neural patterns within each visual area in response to visual stimuli. The results show that the mapping is a semi-angle preserving map and the cumulative distribution function of BC can distinguish the local changes to visual areas within and across subjects.

FIG. 1 illustrates an overall processing pipeline 100 for sensory mapping to a cortical surface, and Beltrami coefficient map visualization for visual cortical areas, in accordance with some embodiments. Referring to FIG. 1, in step 110, a patient is subjected to sensory stimuli. In step 115, functional magnetic resonance imaging (fMRI) data is collected for the patient subjected to the sensory stimuli. In step 120, cortical maps are output from the fMRI for processing in stage 135. The cortical maps may refer to visual area cortical maps. This cortical map gives the cortical position inside the visual area for every point in the visual field. The cortical maps of step 120 may be functional MRI activation maps, which capture the activated regions (or points) in 3D volume space as a result of visual stimuli (rings, wedges) presented in the visual field. The brain is located somewhere in this 3D volume space. This cortical map is combined with brain structural scans to project the functional activation data onto the anatomical brain that is also aligned in the same 3D volume space.

In step 125, brain structural MRI scans are performed on the patient. In step 130, the brain structural scans are output for processing stage 135. Brain structural scans are MRI captures of the structural anatomy (shape, folds, cavity) of the brain. These scans do not include cortical activation data projected onto the surface In processing stage 135, the visual cortical maps from step 120 and the brain structural scans from step 130 are retrieved and normalized by one or more electronic processors. In this regard, the electronic processor conformally maps visual cortical surfaces to a topological disk where local geometry structures are well preserved. Then the electronic processor smooths the retinotopy data on the disk domain using a robust data smoothing method that generates a curve that best fits the retinotopy data and eliminates noisy outliers. Then, the electronic processor fits this curve with a piecewise polynomial B-spline function with an adjustable curve smoothness parameter to allow manual control in refining the curve to optimally fit the data while maintaining curve convexity.

In processing stage 135, the electronic processor also determines a Beltrami coefficient for each point location ($x_i$) in the observer's visual field (in the disk domain) that corresponds to a point location (1 to 1 correspondence) in the cortical map (also in the disk domain). The unit of representation for these points is dependent on the resolution of the sensors. For example, it may be a cluster of N pixels after normalization. Here the visual field can be replaced with a number of other sensory spaces such as auditory, somatosensory, or olfactory as long as the domain can be clearly established. Each Beltrami coefficient represents a complex distortion measure for representing data of a location ($x_i$) in the visual field (disk domain) in a shifted location of the cortical map (disk domain) of the patient. The visual field itself is a continuous space. It is divided into processing regions within the brain (i.e. the left half of visual field is processed by V1 in the right hemisphere and the right half by V1 in the left hemisphere).

Figure 10:
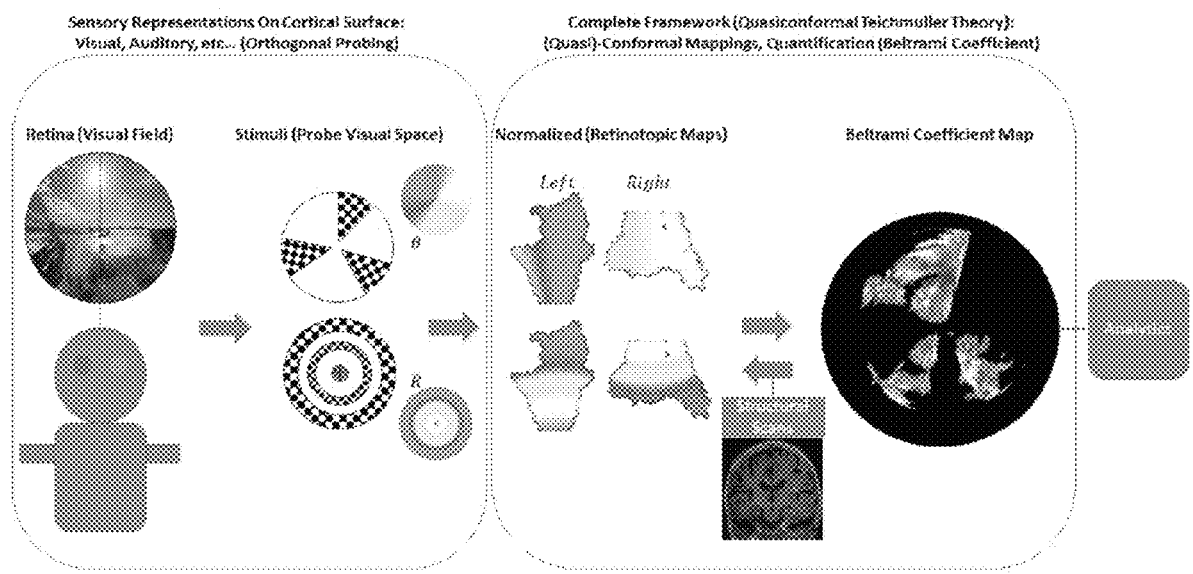
FIG. 10 illustrates the overall processing pipeline described with respect to FIG. 1, in accordance with some embodiments.

In step 140 the electronic processor outputs a Beltrami coefficient map for each point in the sensory space disk domain, which is a mosaic representation of the original sensory image in the sensory field of the cortex. In step 145 the Beltrami coefficient map is analyzed by directly comparing its value everywhere or its statistical distribution over the visual field disk domain with other individual's Beltrami coefficient map or to a normalized template. See FIG. 10 for a visual representation of the overall processing pipeline described with respect to FIG. 1.

FIG. 2 illustrates an overall pipeline 200 for sensory map decoding with Beltrami coefficient map visualization, in accordance with some embodiments. In step 210, task based fMRI experimental measurements are collected. In step 220, visual field sensory stimuli fMRI data is input to processing stage 230. In step 225, MRI sensory area data is input to processing stage 230. In processing stage 230, a Beltrami coefficient map is generated that will produce a Beltrami coefficient value µ for every point in the visual field space (in the disk domain) as a result of processing the correspondence between visual field sensory stimuli (τ) including checkerboard rings and wedges and measured sensory area brain signals (ω) in a common disk space 240. In step 235, a Beltrami coefficient map is output from the process 230.

FIG. 3 illustrates an overall pipeline 300 for brain sensory field decoding with Beltrami coefficient map visualization, in accordance with some embodiments. As noted above, the Beltrami coefficient map represents a function where the input domain includes locations in the visual field and the output is a complex distortion measure at these locations for a patient (or subject). This Beltrami coefficient map function is invertible in that given the boundaries and the Beltrami map of a flattened cortical region, the exact corresponding visual field can be reconstructed. Referring to FIG. 3, at step 310, a patient is subjected to a sensory image. In step 315, new brain signals of the patient are measured in an fMRI system during viewing of the sensory image. In step 320, the new sensory area brain signals are input into processing stage 335. In stage 325 a previously recorded Beltrami map for the patient is retrieved. In step 330, Beltrami coefficients from the previously recorded Beltrami map are input to processing stage 335. In processing stage 335, data for a visual field corresponding to the new brain signals is generated based on the new sensory area brain signals and inverted function of the Beltrami map using the linear Beltrami solver. In step 345, data representing each location of the visual field is output from the processing stage 335.

Figure 4A:
FIGS. 4A-4F illustrate resulting functional data projected onto the cortical surface, in accordance with some embodiments.
Figure 4B:
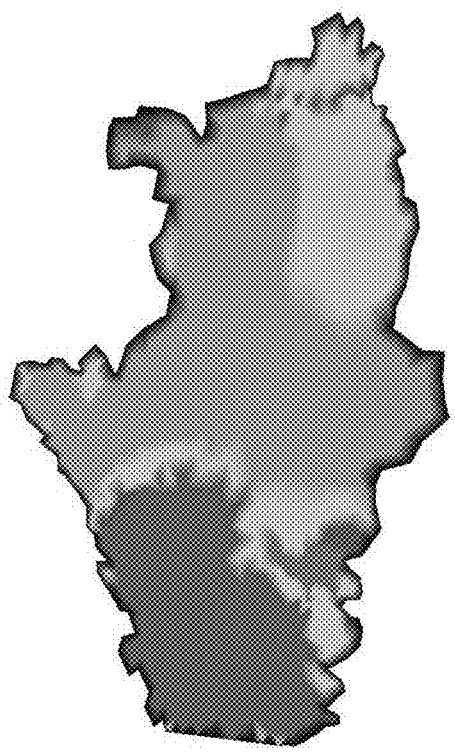
Figure 4C:
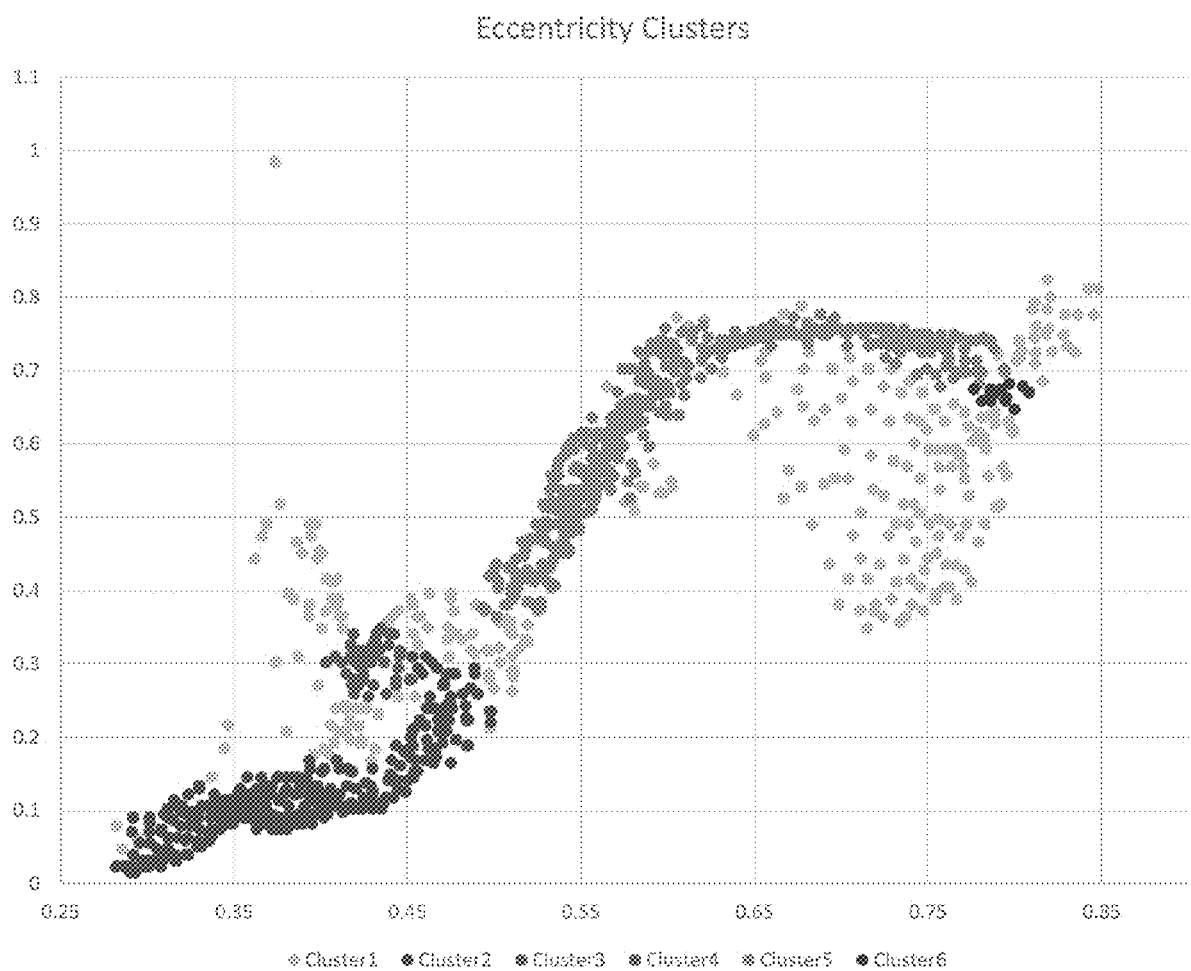
Figure 4D:
Figure 4E:
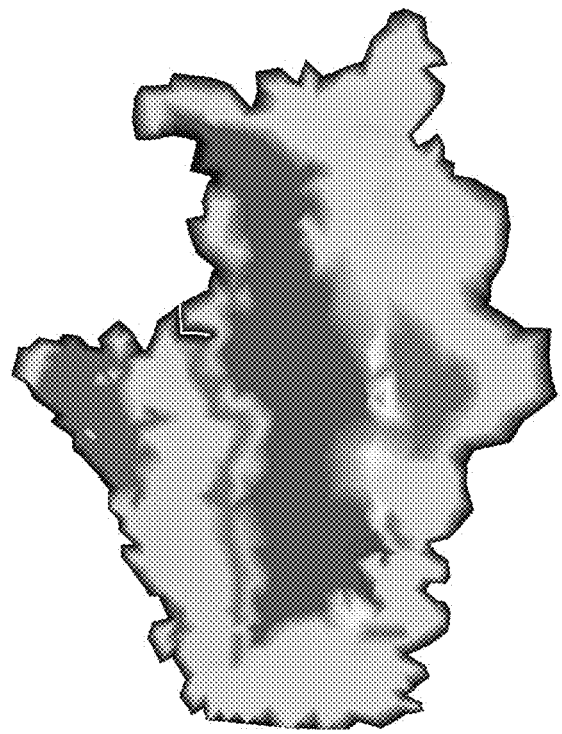
Figure 4F:
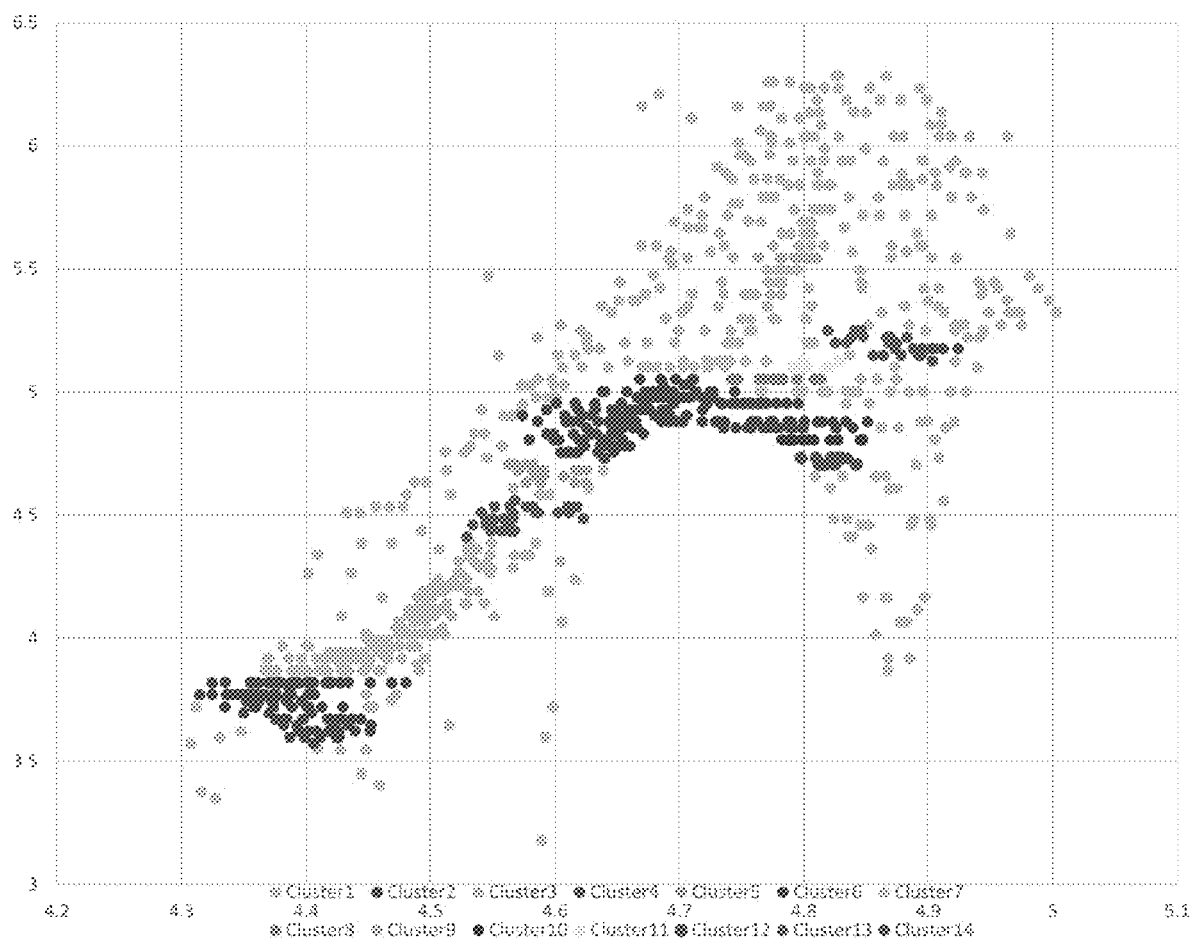

This disclosure also addresses artifacts in traveling wave data and preprocessing steps to eliminate the artifacts. FIGS. 4A-4F illustrate resulting functional data projected onto the cortical surface for one subject. FIG. 4A illustrates function data projected onto the cortical surface for an expanding ring stimulus (eccentricity data). FIGS. 4B and 4C illustrate clustering results for the functional data shown of FIG. 4A for eccentricity. FIG. 4B is the clustering results from FIG. 4C projected back onto the mesh by point correspondence. FIG. 4D illustrates function data projected onto the cortical surface for rotating wedge stimulus (polar angle). FIGS. 4E and 4F illustrate clustering results for the functional data shown in FIG. 4D for polar angle. FIG. 4E is the clustering results from FIG. 4F projected back onto the mesh.

Referring again to FIG. 4A, the image in FIG. 4A represents a traveling wave of activation on the cortical surface that is elicited by visual stimuli comprising a checkerboard pattern including expanding rings. FIG. 4D illustrates a traveling wave of activation on the cortical surface that is elicited by visual stimuli comprising a checkerboard pattern including rotating wedges. Although the traveling wave pattern is always discernible with properly collected data, many artifacts are still present that make it extremely difficult for data analysis. Typically, the data is aggregated across subjects and registered to a template before it is fitted with some mathematical function that best describes the resulting data. Although aggregation can remove noise in the data, it can also cause information loss. Therefore, in this disclosure, the data is not aggregated. Instead, the data points are clustered to determine which group of functional data points in the primary visual cortex best represents the traveling wave pattern. A model is then fitted to the clusters that best describes the traveling wave data. Missing data is then filled in and inconsistent data are revised to form a more complete and consistent dataset for analysis.

As noted above, FIGS. 4A and 4D show the traveling wave functional data for expanding ring stimulus (FIG. 4A) and rotating wedge (FIG. 4D) relative to their clustering results for one subject. For the expanding ring stimulus (FIGS. 4B-4C), clusters colored blue and orange clearly present an increasing traveling wave of activation pattern in the radial direction starting at the bottom. As the radial distance on the cortical surface (x-axis) increases, the color mapping of the functional data to the visual field radial distance (y-axis) also increases. Similarly, for the rotating wedge stimulus (FIGS. 4E-4F), clusters colored blue, light green, dark green, light pink, and red also present an activation pattern in an angular direction sweeping from left to right. As the angular distance increases sweeping from left to right on the cortical surface (x-axis), the color mapping of the functional data to the visual field angular distance (y-axis) also increases.

The clusters that best represent the traveling wave pattern are then fitted using B-spline curves since there is no premise for choosing a particular function for the traveling wave data. Each B-spline curve is manually adjusted for best fit versus smoothness of the curve. Smoothness is set to as high as possible as long as the R-squared value of the fit is reasonably maintained. FIGS. 5A-5F illustrate measured retinotopic data for eccentricity (FIG. 5A) and polar angles (FIG. 5D) that are smoothed using B-spline curve fitting (FIGS. 5B and 5E respectively). The colored data encodes the stimulus location within the visual field that activated that particular cortical location. Using the colored data, the cortical mesh is homeomorphically transformed to visual field space to form another mesh (FIGS. 5C and 5F respectively). The Beltrami coefficient is then used to compare the original cortical mesh and its counterpart in the visual field.

FIGS. 5A-5F show the resulting B-spline curves for expanding ring (FIG. 5A) and rotating wedge (FIG. 5B) stimulus of one subject. The table of images, FIG. 5A-5B, provides a summary of all the smoothness and R-squared values of the fit obtained for all subjects. The right hemisphere for a subject 5, had a very unique artifact that could not be resolved using density based clustering. The clusters that follow a particular activation pattern were not separable from a cluster that reversed the order sequence of the traveling wave. As a result, the curve fitting had to include the artifact cluster and resulted in an R-squared value that is much lower than the rest.

After fitting the functional data with a B-spline curve, the color value at every point in the primary visual cortex was updated with its fitted value. FIGS. 5B and 5E show the smoothed version of the functional data in FIGS. 5A and 5D, respectively. Decoding the color data at each point on the cortical surface gives the stimulus location within the visual field that activated the BOLD signal there. Then each point on the cortical surface is shifted to its stimulus location in the visual field to create the topologically equivalent representation of the primary visual cortex shown in FIGS. 5C and 5F.

Figure 6:
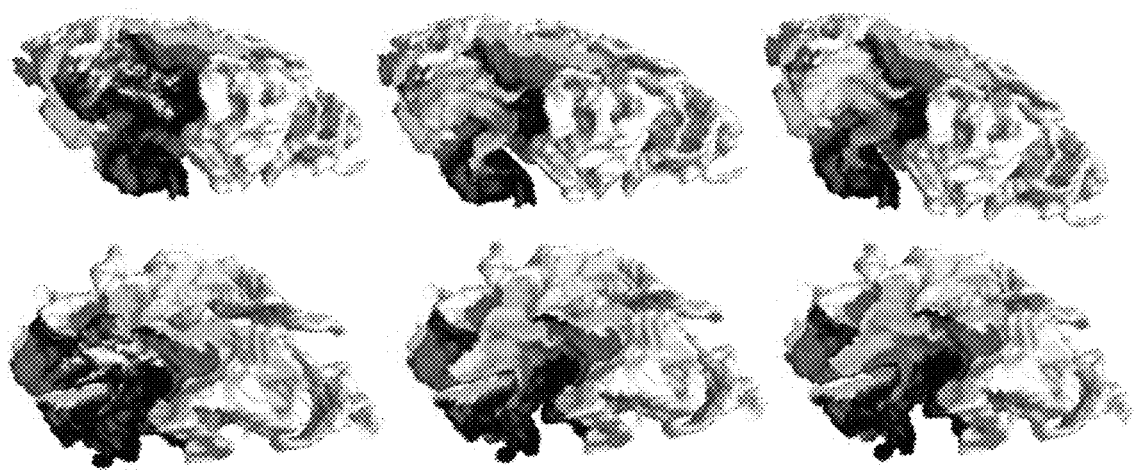
FIG. 6 illustrates a Beltrami map for primary visual cortex (V1) projected back onto the original cortical surface, in accordance with some embodiments.

FIG. 6 illustrates a Beltrami map for primary visual cortex (V1) projected back onto the original cortical surface. This visualization provides a 3 dimensional perspective of where the measured distortions are located within the structural anatomy of this particular brain. It is useful if precise physical interactions with this region are required, such as electrical stimulations or attachment of a medical device. Projecting the various measurements and maps made in the processing pipeline back to the 3 dimensional brain surface is always possible because the original brain anatomy data and subsequent processing are always preserved in memory with the implementation of this system.

This disclosure utilizes Beltrami coefficient (BC) maps. The BC for the primary visual cortex (V1) was computed for each subject. The BC is computed per vertex on the discrete surface mesh representation of the cortical surface. Collectively, the BC of each surface is a map that describes the local angle-angle preserving property of each individual retinotopy. This is the BC map. A QC map is reconstructed using only the BC map that was measured using the best fit approximation of the original retinotopic data. Globally, the BC can be represented using the Beltrami differential (BD). According to QC Teichmuller theory, there is a one-to-one correspondence between the set of BD and the set of QC surface mappings under normalization conditions. Therefore, every QC surface mapping can be fully determined by the Beltrami differential and reconstructed by solving the Beltrami equation. If BC maps are similar across subjects, we can use an average BC map as a template for reconstructing a QC map for a subject that we do not have retinotopic data for. This QC map is a good initial estimation of what the subject's retinotopic map would look like if travelling wave data was collected.

Figure 11:
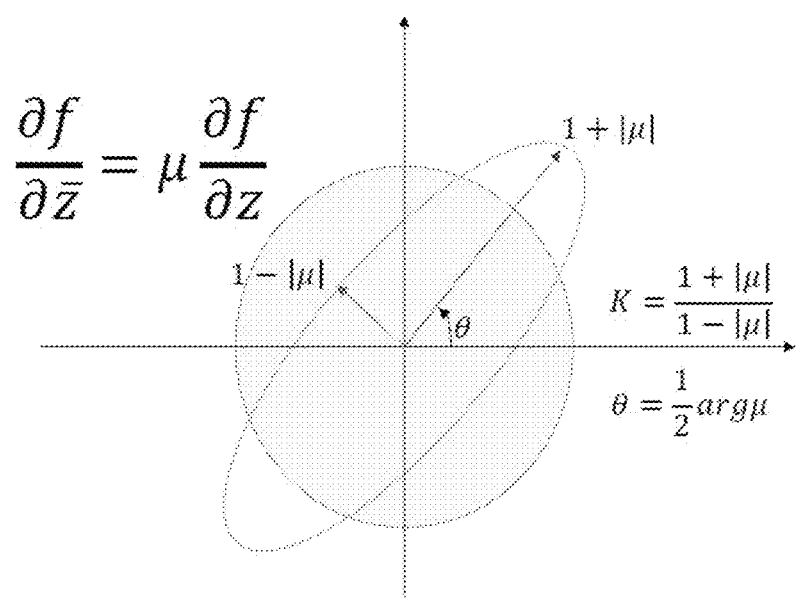
FIG. 11 illustrates a Beltrami coefficient map and method for determining a dilation value, in accordance with some embodiments.
Figure 11:
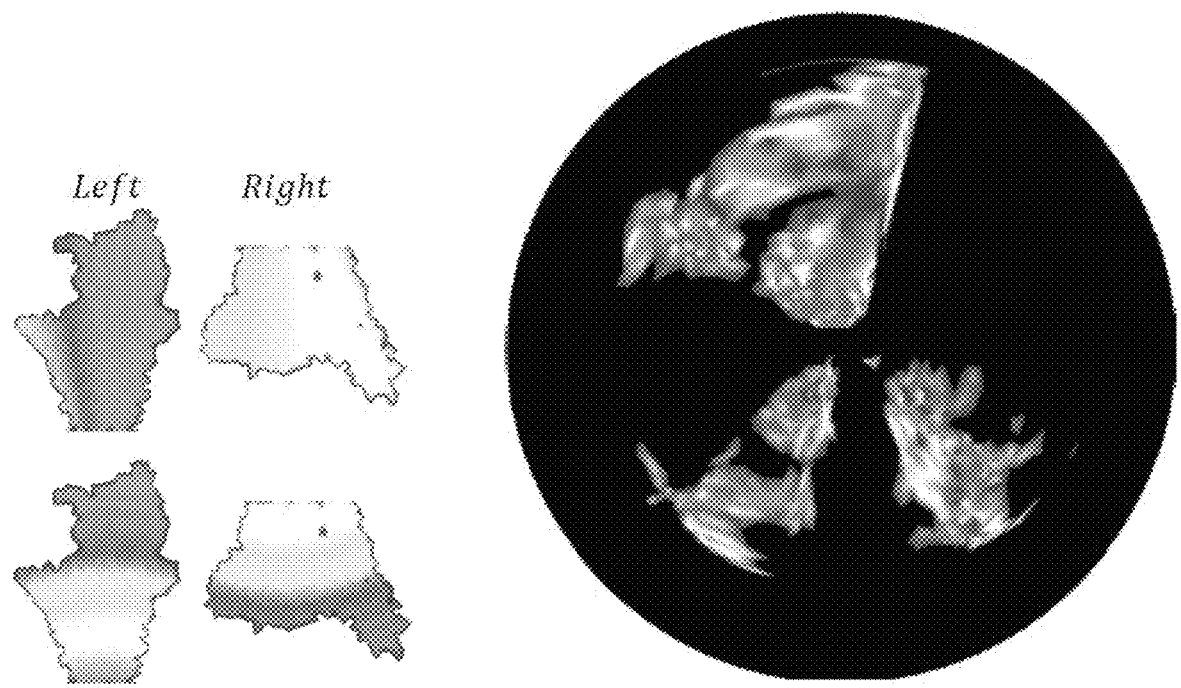

This disclosure also addresses comparing Beltrami coefficient distribution across subjects using angular distortion. Subjects were compared by directly measuring angle distortion of each subject's retinotopic map. Given two surfaces, if transforming one into the other or vice versa via continuous bending and stretching is possible then they are considered homeomorphic to each other. The Beltrami coefficient for every data point on the primary visual cortex was directly computed and the cumulative distribution function (CDF) for the dilation values was computed. The dilation K is related to the Beltrami coefficient by the following formula $K=(1+|\mu|)/(1-|\mu|)$, where $\mu$ is the Beltrami coefficient. The set of BC for every point on the discrete surface forms a 'BC Map' that fully determines a QC surface mapping. See FIG. 11 that illustrates an example Beltrami map and determination of dilation K.

Figure 7:
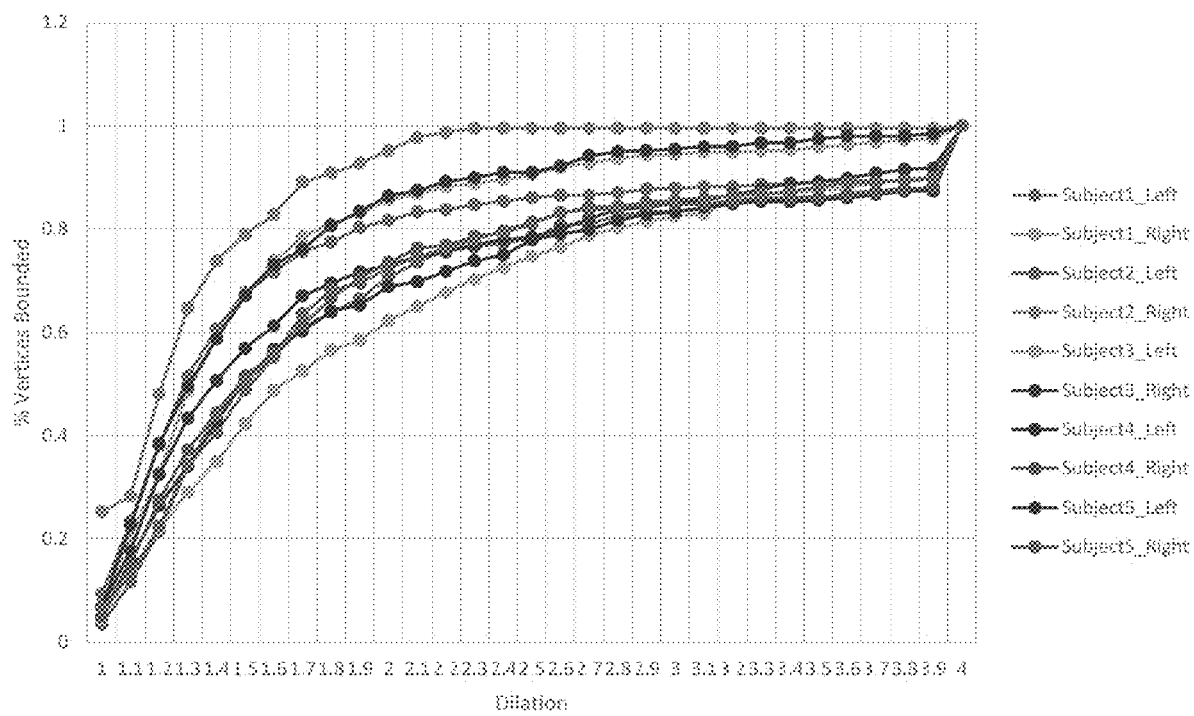
FIG. 7 graphically illustrates the cumulative distribution function (CDF) of dilation values versus percentage of points on the discrete surface bounded for five subjects, in accordance with some embodiments.

FIG. 7 shows the CDF for five subjects. The percentage of measured vertices that are bounded by dilation values are plotted for increasing dilation values on the x-axis. The difference between two CDFs can be defined as the difference between the area under the curve up to bounded dilation value. They are also directly observable by comparing the rising steepness of the CDFs as dilation increases. Steeper slopes indicate retinotopic mappings that are more conformal. The primary visual cortex CDF of each of the five subjects was analyzed for foveal eccentricity up to three degrees and it was observed that on average, 36.5% of vertices were not bounded by 1.5 dilation (min=17.2%, max=51.3%, average=36.5%). These results indicate that retinotopic maps are likely not conformal and are more likely QC. Although the discrete conformal flattening algorithm also introduced some distortion due to imperfect minimization of the discrete energy term, the percentage of vertices not bounded is much larger than those typically observed with conformal mappings.

Beltrami Coefficient maps may be inverted to reconstruct an original sensory field. A Beltrami coefficient map describes the local distortion from an ideal conformal mapping. Theoretically, it uniquely determines the mapping so it provides an opportunity to reconstruct the mapping between the retina and cortical visual area. Specifically, one can compose a set of linear equations described in current literature as Linear Beltrami Solver with the Beltrami coefficient map values and the boundary of the shape as the known parameters, and the corresponding locations of points in visual field as the unknowns. Solving the linear equations will generate a quasiconformal mapping of the current cortical visual area shape that is a reconstruction of the original images on the retina. We call this process an inversion. The inversion process can reconstruct what is in a person's sensory field by analyzing brain changes captured by fMRI. (See the flow chart in FIG. 3)

A preprocessing method and system includes robust data smoothing to extract a smooth curve representation of traveling wave pattern and remove outliers. The curve fitting is data driven and relies on consistent traveling wave data. Piecewise polynomial B-spline curve fitting is then applied to the curve with a smooth term that is controlled manually by the user to best fit the data while ensuring that the curve is convex. The preprocessing methodology resolved the functional data artifacts typical with many retinotopic data. The retinotopic maps are studied using Riemann mapping theorem for surfaces by computing the set of Beltrami coefficients (BC) for every vertex in the measured visual area. The BC fully captures the properties of the mapping and can be used as a template to reconstruct individual sensory maps using quasiconformal maps. It is a rigorous model of the expected neural patterns within each visual area in response to sensory stimuli. The software tools were combined into a complete framework for measuring and reconstructing individual retinotopic maps. It first constructs an angle preserving mapping from the cortical surface to the planar disk domain. Second, it measures the conformality of the cortical planar surface with respect to the reconstructed visual field surface. The visual field surface is a transformation of the cortical planar surface to visual field space without altering the topology. The best fit fMRI travelling wave data was used to direct the transformation coordinates. Third, the angle distortions were measured by computing the BC everywhere (at every point) between the two surfaces. The final result is a collection of angle distortion measures (BC maps) that can be averaged to create templates for building unique QC maps using QC Teichmuller Theory. Since all the essential properties of the surface mapping are captured by the BC, the QC map provides a unique geometric description of individual retinotopy. With this framework, it was directly shown that retinotopic mapping is a QC map. It also was shown how the cumulative distribution function of BC is a novel way to concisely capture individual retinotopic maps and how it can be used for comparison across subjects.

Usage of the Beltrami coefficient measurements for analyzing functional data of retinotopically organized regions is an improvement over prior works and implementations attempting to describe the relationship between changes in the visual field and their corresponding mosaic representation on the cortical surface. In prior implementations, the models are controlled by only a few parameters (2 to 4) and so adjusting them will globally affect the predictions for every other point in the model also. This has several limitations. First, the model cannot be updated for a particular region after collecting more experimental data there. Second, it is only possible to fill in regions with missing data from a global context and not possible to take advantage of local distortions of adjacent regions. In our implementation, the Beltrami coefficient measurement considers the intrinsic properties of the cortical surface which makes it sensitive to local changes. The conformality of retinotopic mappings is directly measurable from the data. The embodiments of the present disclosure are controlled by a greater set of parameters (each Beltrami coefficient is a parameter and each visual area can have several thousands of them). Furthermore, small patches of sub-regions on the cortex are locally adjustable by adjusting the Beltrami coefficient values within it. The region external to the sub-region is unaffected.

We now turn to materials and methods used for quantification of the mapping of the sensory areas of the brain. This disclosure addresses collecting retinoptopic functional data. Task activated functional MRI data of the primary visual cortex was collected for five subjects using standard travelling-wave experimental procedures. Visual stimuli included rotating wedges and expanding rings comprised of black and white checkerboard patterns that elicit an ordered sequence of neural activity in the visual cortex. The resulting activity pattern sweeps across the retinotopically organized regions of the visual cortex along iso-angle and iso-eccentricity and is commonly referred to as the "traveling wave." Activated neurons with a BOLD signal that is above threshold are colored using a 256 color map according to the stimulus location in the visual field that activated them. Both structural MRI and functional MRI scans were conducted using a 3.0T scanner. The primary visual cortex was manually labeled by experts using known anatomical landmarks and phase reversals of functional data that occurs near the boundaries between early visual areas.

Figure 8A:
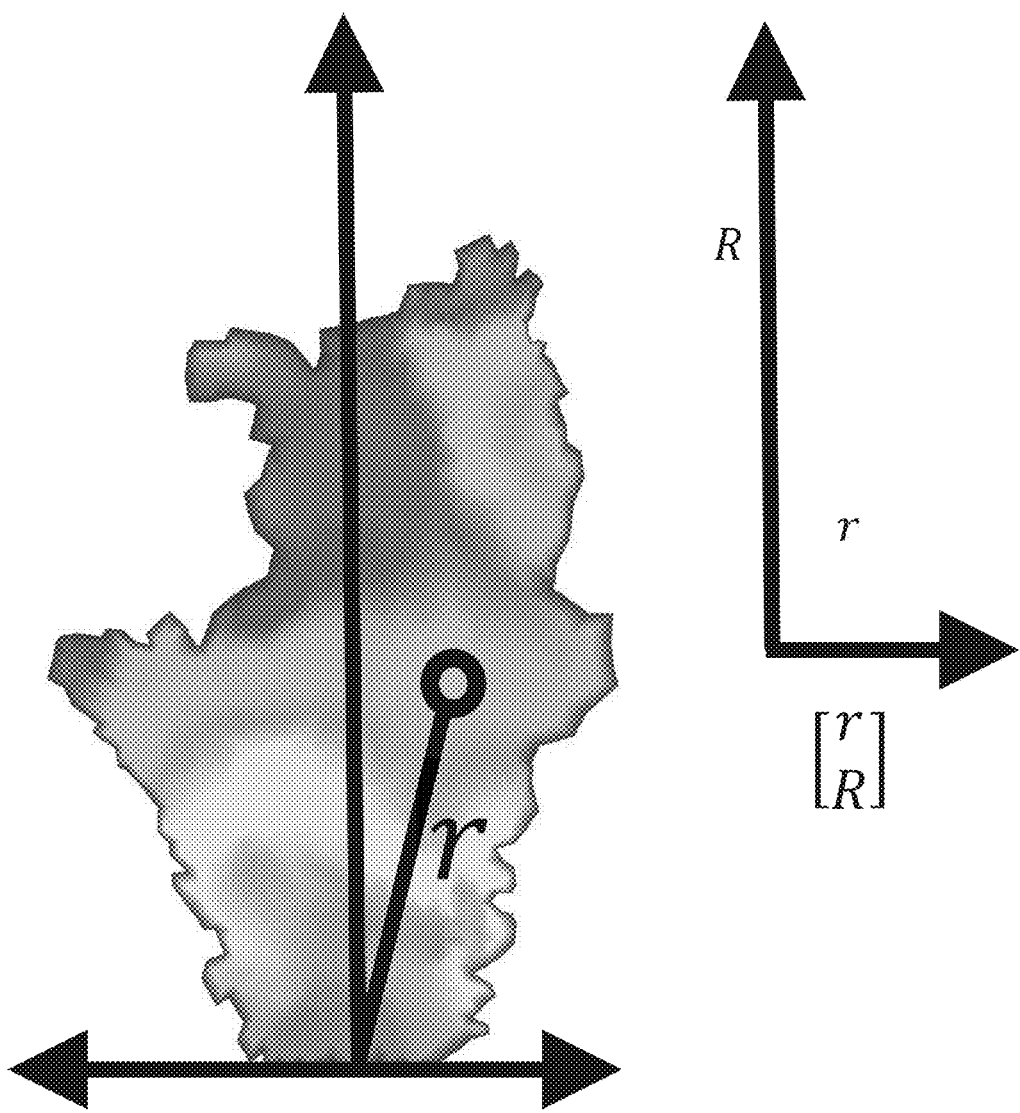
FIGS. 8A-8D illustrate decoding and plotting radial and angular data points for clustering, in accordance with some embodiments, in accordance with some embodiments.
Figure 8B:
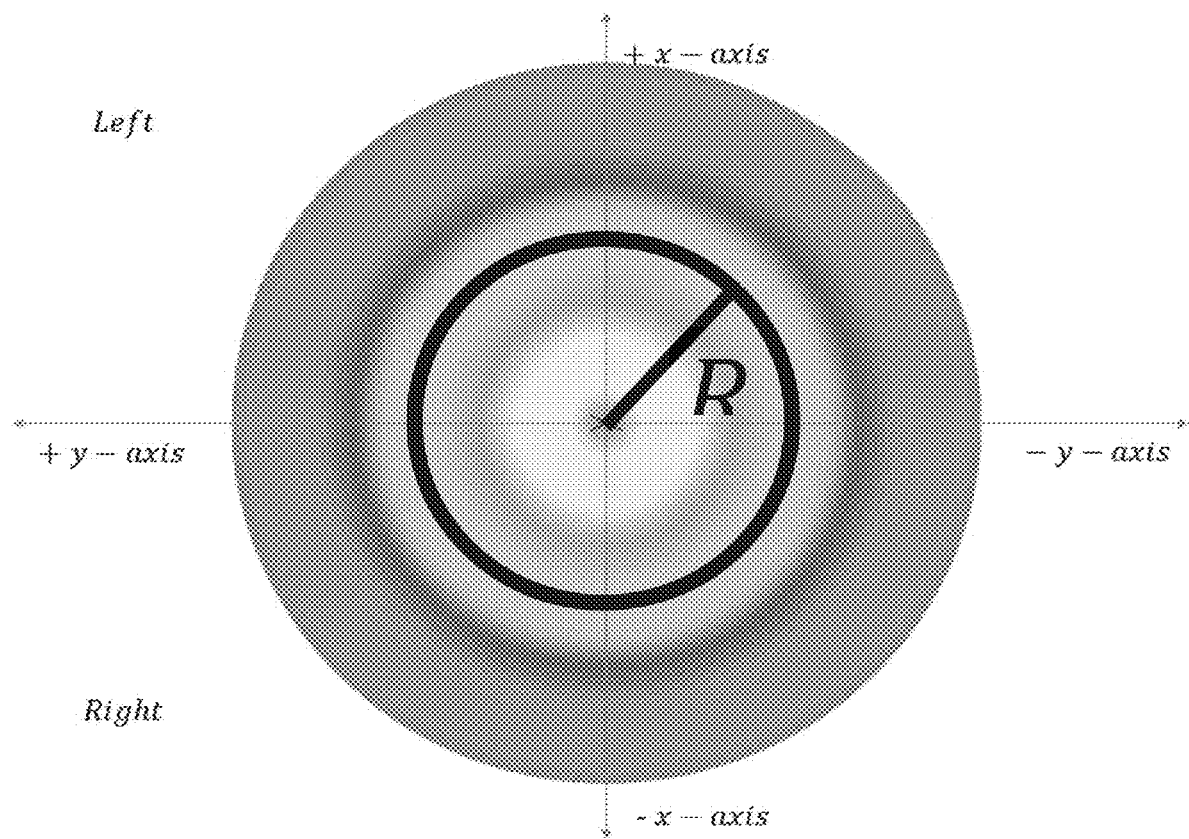
Figure 8C:
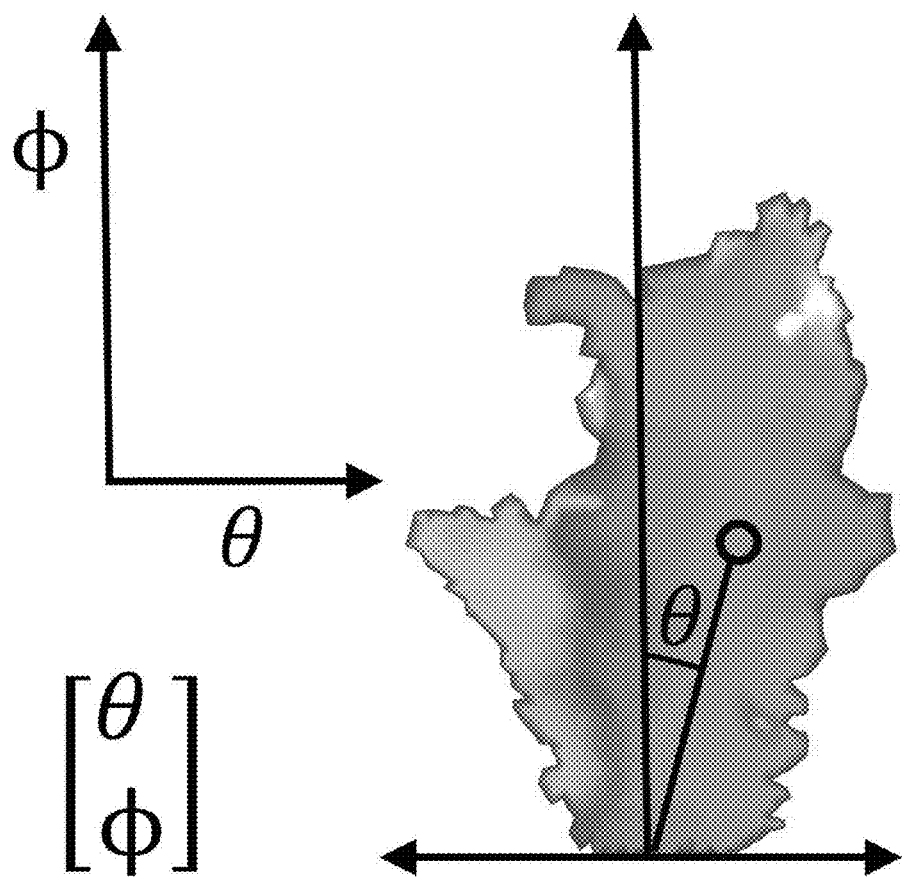
Figure 8D:
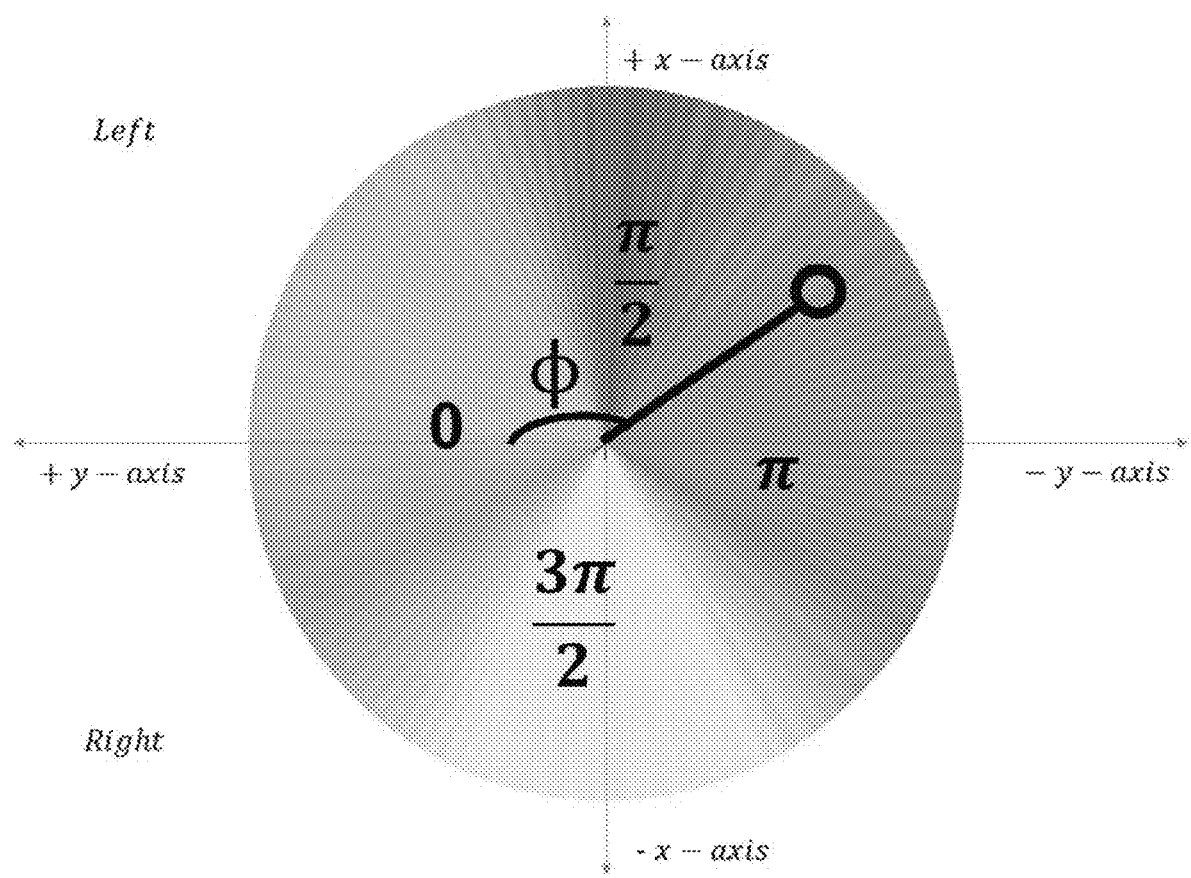
Figure 9:
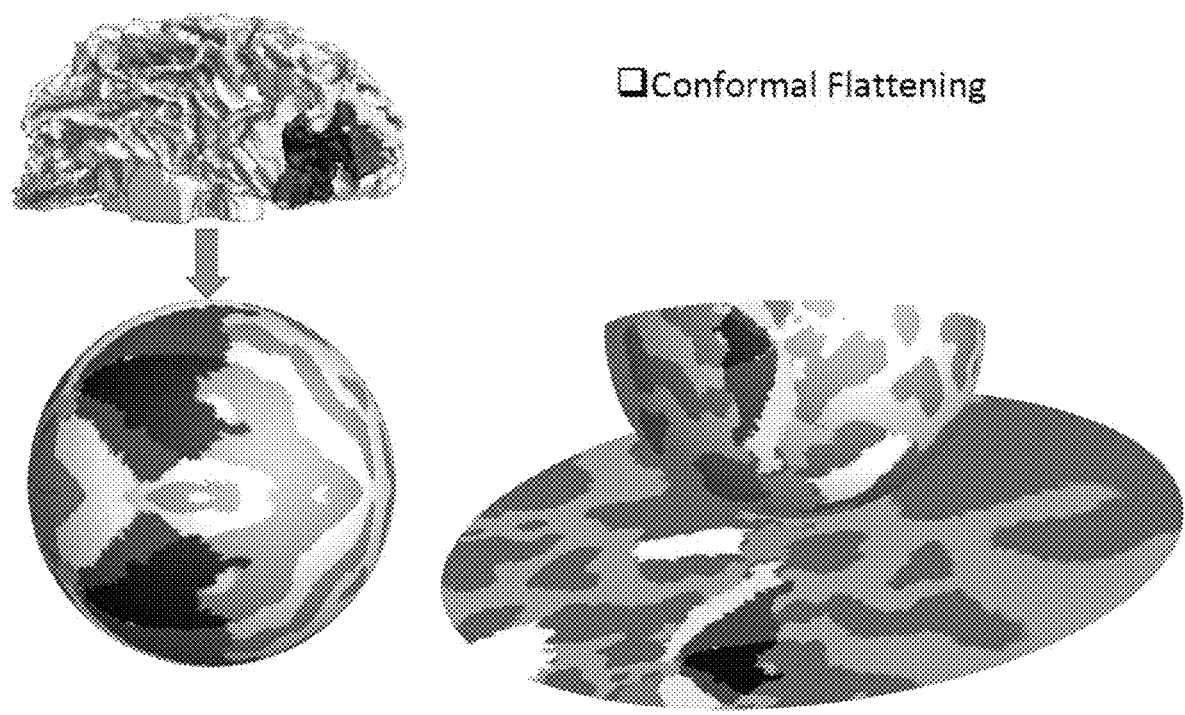
FIG. 9 that illustrates an example of conformal flattening of a cortical surfaced, in accordance with some embodiments.

Conformal flattening of primary visual cortex, alignment, and functional data decoding was performed. The cortical surface was conformally flattened to a unit disk using a spherical conformal mapping method. See FIG. 9 that illustrates an example of conformal flattening of a cortical surfaced. As shown in FIG. 9, the cortical surface is unfolded to form a sphere that is flattened to form the unit disk. Next, a wedge from the unit disk that contains primary visual area V1 was removed. The wedge was aligned so that its tip is at the origin and the wedge was located completely within the right or left visual hemifield. Color encoded functional data of ring (eccentricity) and wedge (polar angle) stimulus is then decoded and recorded for every point in the labeled primary visual cortex. Decoding is shown in FIGS. 8A and 8B for eccentricity and FIGS. 8C and 8D for polar angle.

Decoded functional data was plotted. Every point on the cortical surface was plotted using its radial or angular distance to its location on the cortical surface as the independent variable and its location in the visual field as the dependent variable. FIGS. 8A-8D illustrate how radial and angular distances are computed and plotted.

Functional data was clustered. The density-based spatial clustering of applications with noise (DB SCAN) was used to cluster the data. It is a popular type of data clustering algorithm that groups points together based on how closely they are packed within a specified neighborhood (density-based). Its advantage over other clustering algorithms such as k-means is that it can find clusters that have non-linear boundaries and does not require the number of clusters upfront. Additionally, it is robust to outliers and is mostly insensitive to the ordering of the points in the dataset. The algorithm considers points, clusters, and reachability. Points can be a core point, reachable, or outliers. Clusters are formed based on rules with respect to the reachability of core points and non-core points. The two parameters required by the algorithm: $\epsilon$ and minPts are easily chosen if the data is well understood. Basic statistics can be computed to understand the distribution of the data first before choosing the parameters. Then fine tuning of the parameters is required to obtain the best clustering. The $\epsilon$ parameter defines the neighborhood size while minPts define the minimum number of points in a cluster (minimum cluster density). The DB SCAN package was used for clustering the data.

B-splines were used for data curve fitting. The data using B-spline curves was fitted because there is no premise for choosing a particular function. B-splines are composed of a set of control points that control the polynomial curves joined to form the whole curve. A smoothness requirement was added that can manually adjust to limit overfitting and concavity. Adjustments are made by selecting how much to linearly interpolate between fitting the data versus smoothness. Care should be taken when fitting data. Although fitting can be attempted on any data set, if the majority of the data is inconsistent, then the results are not going to be meaningful. If the data does not exhibit the traveling wave activation pattern then the functional data should be discarded and the traveling wave experiment repeated.

The Beltrami coefficients were determined. The Beltrami coefficient was calculated to measure the angle preservation property of the two homeomorphically mapped surfaces. If the mapping is conformal the local distortion at each point will be zero and the dilation measurement will be one. They are related by the formula $K=(1+|\mu|)/(1-|\mu|)$, where K is dilation and $\mu$ is the Beltrami coefficient. In practice, brain surfaces are typically represented with triangular meshes because many of the widely used computational algorithms operate on them. The details of computing the Beltrami coefficient for triangular mesh surfaces described in Ta D, et al. (2014) Characterizing human retinotopic mapping with conformal geometry: a preliminary study, in Medical Imaging: Image Processing. p. 90342A, which in incorporated herein by reference.

Figure 12:
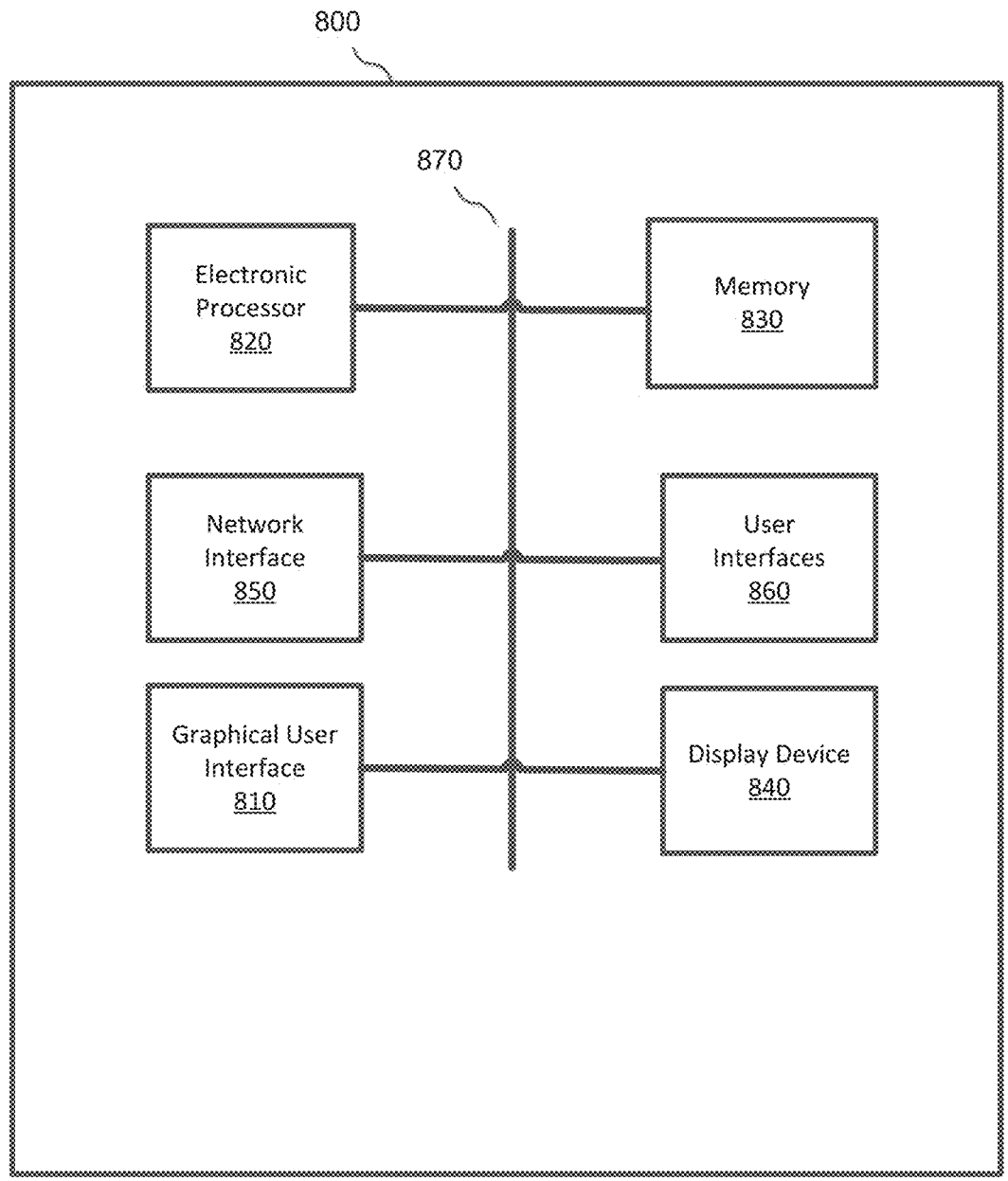
FIG. 12 is a block diagram of a system that is provided for quantifying the mapping of the sensory areas of the brain, in accordance with some embodiments.

FIG. 12 is a block diagram of a system that is provided for quantifying the mapping of the sensory areas of the brain. The system includes, among other things, a computer system 800, a graphical user interface 810, an electronic processor 820, a memory 830, a display device 840, a network interface 850, user interfaces 860 and an communication bus 870.

In some embodiments, the electronic processor 800 may be communicatively coupled to, the graphical user interface 810, the electronic processor, the memory 830, the display device 840, the network interface 850 and the user interfaces 860 via the communication bus 870.

The memory 830 may store program instructions that when executed by the electronic processor 820 may cause the electronic processor to perform quantification of the mapping of the sensory areas of the brain, according to the embodiments.

In various embodiments, the electronic processor 820 may be a uniprocessor system including one electronic processor, or a multiprocessor system including several electronic processors (e.g., two, four, eight, or another suitable number). Electronic processors may be any suitable processor capable of executing instructions. For example, in various embodiments, the electronic processors may implement any of a variety of instruction set architectures (ISAs), such as the x86, PowerPC, SPARC, or MIPS ISAs, or any other suitable ISA. In multiprocessor systems, each of the electronic processors 338 may commonly, but not necessarily, implement the same ISA.

In some embodiments, at least one electronic processor 820 may be a graphics processing unit. A graphics processing unit or GPU may be considered a dedicated graphics-rendering device. Modern GPUs may be very efficient at manipulating and displaying computer graphics, and their highly parallel structure may make them more effective than typical CPUs for a range of complex graphical algorithms. For example, a graphics processor may implement a number of graphics primitive operations in a way that makes executing them much faster than drawing directly to the screen with a host central processing unit (CPU). In various embodiments, the image processing methods disclosed herein may, at least in part, be implemented by program instructions configured for execution on one of, or parallel execution on two or more of, such GPUs. The GPU(s) may implement one or more application programmer interfaces (APIs) that permit programmers to invoke the functionality of the GPU(s). Suitable GPUs may be commercially available from vendors such as NVIDIA Corporation, ATI Technologies (AMD), and others.

The memory 830 may be configured to store program instructions and/or data and accessible by the electronic processor 820. In various embodiments, the memory may be implemented using any suitable memory technology, such as static random access memory (SRAM), synchronous dynamic RAM (SDRAM), nonvolatile/Flash-type memory, or any other type of memory. In the illustrated embodiment, program instructions and data implementing desired functions, such as those described above for various embodiments, are stored within the memory 830 as program instructions and data storage. In other embodiments, program instructions and/or data may be received, sent or stored upon different types of computer-accessible media or on similar media separate from the memory. Moreover, in some embodiments, a database that is accessible via the network interface may store, among other things, data for implementing desired functions, such as those described above for various embodiments. Generally speaking, a computer-accessible medium may include storage media or memory media such as magnetic or optical media, e.g., disk or CD/DVD-ROM coupled to computer system via I/O interface. Program instructions and data stored via a computer-accessible medium may be transmitted by transmission media or signals such as electrical, electromagnetic, or digital signals, which may be conveyed via a communication medium such as a network and/or a wireless link, such as may be implemented via network interface.

In one embodiment, communication bus 870 is coupled between the electronic processor 820, system memory 830, the graphical user interface 810, and any peripheral devices in the computer system 800, including network interface 850 or other peripheral interfaces, such as display interface 840 and user interfaces 860. In some communication bus 870 may perform any necessary protocol, timing or other data transformations to convert data signals from one component (e.g., the memory) into a format suitable for use by another component (e.g., processor). In some embodiments, the communication bus 870 may include support for devices attached through various types of peripheral buses, such as a variant of the Peripheral Component Interconnect (PCI) bus standard or the Universal Serial Bus (USB) standard, for example. In some embodiments, the function of the communication bus 870 may be split into two or more separate components, such as a north bridge and a south bridge, for example. In addition, in some embodiments some or all of the functionality of the communication bus 870, such as an interface to memory, may be incorporated directly into the processor 820.

The network interface 850 may be configured to allow data to be exchanged between the computer system 800 and other devices attached to a network, such as other computer systems, a database, imaging devices or other medical devices, such as an MRI system. In various embodiments, network interface may support communication via wired or wireless general data networks, for example: via telecommunications/telephony networks such as voice networks or digital fiber communications networks; via storage area networks such as Fiber Channel SANs, or via any other suitable type of network and/or communications protocol.

The user interfaces 860 may support, in some embodiments, one or more of display terminals, keyboards, keypads, touchpads, scanning devices, voice or optical recognition devices, or any other devices suitable for entering or retrieving data by a user. Multiple user input/output devices may be present in the computer. In some embodiments, similar input/output devices may be separate from the computer and may interact with other devices through a wired or wireless connection, such as over network interface.

Those skilled in the art will also appreciate that, while various items may be stored in memory 830 while being used, these items or portions of them may be transferred between memory 830 and other storage devices for purposes of memory management and data integrity. Alternatively, in other embodiments some or all of the software components may execute in memory on another device and communicate with the illustrated system via inter-computer communication. Some or all of the system components or data structures may also be stored (e.g., as instructions or structured data) on a computer-accessible medium or a portable article to be read by an appropriate drive, various examples of which are described above. In some embodiments, instructions stored on a computer readable medium separate from the system may be transmitted to the system via transmission media or signals such as electrical, electromagnetic, or digital signals, conveyed via a communication medium such as a network and/or a wireless link. Various embodiments may further include receiving, sending or storing instructions and/or data implemented in accordance with the foregoing description upon a computer readable medium. Accordingly, the present embodiments may be practiced with other computer system configurations.

Various embodiments may further include receiving, sending or storing instructions and/or data implemented in accordance with the foregoing description upon a computer readable medium. Generally speaking, a computer readable medium may include storage media or memory media such as magnetic or optical media, e.g., disk or DVD/CD-ROM, volatile or nonvolatile media such as RAM (e.g. SDRAM, DDR, RDRAM, SRAM, etc.), ROM, or flash memory, etc., as well as transmission media or signals such as electrical, electromagnetic, or digital signals, conveyed via a communication medium such as network and/or a wireless link.

Various features and advantages of the disclosure are set forth in the following claims.

What is claimed is:

1. A method of quantifying the mapping of sensory areas of the brain, the method comprising:
acquiring functional magnetic resonance imaging data of a patient, the functional magnetic resonance imaging data including sensory data indicating activated regions in 3D volume space of a brain of the patient in response to a visual stimulus;
generating a cortical map by normalizing the sensory data to a structural data of cortical surfaces of the brain;
applying a spherical conformal mapping process to flatten the cortical surfaces in the cortical map to a unit disk;
applying a density-based spatial clustering process to the sensory data in the flattened cortical map to identify clusters that best represent a traveling wave pattern corresponding to the visual stimulus;
fitting the clustered sensory data with one or more B-spline curves;
generating a quasiconformal map by applying data smoothing to the sensory data in the flattened cortical map, wherein generating the quasiconformal map includes adjusting each B-spline curve to increase smoothness of the curve while maintaining an R-squared value of the fit of the sensory data to the B-spline curve;
generating a Beltrami coefficient map based on the quasiconformal map, wherein the Beltrami coefficient map indicates, for each location in the quasiconformal map, a complex distortion measure of a location in the visual field corresponding to the location in the quasiconformal map; and
generating a numerical metric based on the Beltrami coefficient map.

2. The method of claim 1, further comprising applying the Beltrami coefficient map to quantify cortical changes related to sensory and neurological diseases including at least one selected from a group consisting of glaucoma, diabetic retinopathy, age-related macular degeneration, cataract, amblyopia, multiple sclerosis, Alzheimer's disease, Parkinson's disease, traumatic brain injury, stroke, and brain tumor.

3. The method of claim 1, wherein applying the data smoothing to the sensory data in the flattened cortical map includes generating a curve that best fits the sensory data in the flattened cortical map and eliminates noisy outliers.

4. The method of claim 3, wherein generating the quasiconformal map further includes:
fitting the generated curve with a piecewise polynomial B-spline function; and
adjusting a smoothness parameter of the piecewise polynomial B-spline function to optimally fit the sensory data while maintaining curve convexity.

5. A method of reconstructing a new visual stimulus based on captured functional magnetic resonance imaging data, the method comprising:
acquiring new functional magnetic resonance imaging data for the patient, the new functional magnetic resonance imaging data including new sensory data in response to the new visual stimulus;
generating a second cortical map by normalizing the new sensory data to the structural data of cortical surfaces of the brain;
applying the spherical conformal mapping process to flatten the cortical surfaces in the cortical map to a new unit disk;
identifying a wedge from the new unit disk that contains a primary visual cortex area (V1) of the brain; and using the Beltrami coefficient map generated by the method of claim 1 to decode the new sensory data from the wedge of the new unit disk to reconstruct the new visual field stimulus.

6. A method for monitoring vision changes in a patient over time, the method comprising:
   determining a first numeric metric using the method of claim 1 at a first time;
   determining a second numeric metric using the method of claim 1 at a second time, the second time being subsequent to the first time; and
   comparing the first numeric metric and the second numeric metric.

7. The method of claim 6, wherein the second numeric metric is determined after beginning treatment for a disease, and further comprising quantifying progress of the treatment based on the comparison of the first numeric metric and the second numeric metric.

8. The method of claim 6, wherein the second numeric metric is determined after diagnosis of a disease, and further comprising quantifying progress of the disease based on the comparison of the first numeric metric and the second numeric metric.

* * * * *